United States Patent [19]

Hosoi et al.

[11] Patent Number: 5,476,912
[45] Date of Patent: Dec. 19, 1995

[54] SILICONE-MODIFIED ACRYLIC COPOLYMER AND ADHESIVE THEREOF

[75] Inventors: Yasuhiro Hosoi; Osamu Iwamoto; Masataka Himeno, all of Tokuyama, Japan

[73] Assignee: Tokuyama Corporation, Tokuyama, Japan

[21] Appl. No.: 268,321

[22] Filed: Jun. 30, 1994

[30] Foreign Application Priority Data

| Jul. 2, 1993 | [JP] | Japan | 5-164640 |
| Jul. 15, 1993 | [JP] | Japan | 5-175176 |
| Apr. 5, 1994 | [JP] | Japan | 6-067362 |
| Apr. 28, 1994 | [JP] | Japan | 6-091902 |

[51] Int. Cl.$^6$ ............. C08F 230/08; C08F 220/10; C08F 218/12
[52] U.S. Cl. ............. 526/279; 526/328.5; 526/330
[58] Field of Search ............. 526/279, 328.5, 526/330

[56] References Cited

U.S. PATENT DOCUMENTS 4,831,080  5/1989  Blizzard et al. .

5,229,435  7/1993  Sakai et al. ............. 523/105
5,288,827  2/1994  Li et al. ............. 526/279

FOREIGN PATENT DOCUMENTS

| 0049155 | 4/1982 | European Pat. Off. . |
| 0205327 | 12/1986 | European Pat. Off. . |
| 4131089 | 3/1992 | Germany . |
| 9207916 | 5/1992 | WIPO . |

Primary Examiner—Joseph L. Schofer
Assistant Examiner—Wu C. Cheng
Attorney, Agent, or Firm—Sherman and Shalloway

[57] ABSTRACT

An adhesive which exhibits excellent adhesiveness and is capable of firmly adhering an acrylic resin and a silicone rubber together at a temperature of as low as about 20° to 30° C. requiring a time of as short as several minutes. The adhesive is obtained by dissolving in a solvent a novel silicone-modified acrylic copolymer having a polyorganosiloxane with an SiH reaction point on the side chain.

19 Claims, 8 Drawing Sheets

δ (ppm)

SILICONE-MODIFIED ACRYLIC COPOLYMER AND ADHESIVE THEREOF

BACKGROUND OF THE INVENTION

1. Field of the Invention

The present invention relates to a novel silicone-modified acrylic copolymer having a polyorganosiloxane with an SiH reaction point on a side chain thereof, and to an adhesive comprising the above copolymer as a chief component.

2. Description of the Prior Art

Patients who need a denture and, particularly, a full denture, in many cases, are aged persons, and their alveolar ridges must bear an increased occlusion force per a unit area since the bone has generally been resorbed to a conspicuous degree. The mucosa of alveolar ridges becomes thin due to senile atrophy, and the occlusal stress or masticatory pressure is not softened but is directly transmitted to the alveolar bone. Moreover, a thin mucosa disposed between a hard resin denture base and the hard alveolar bone is tightened and gets hurt after every occlusion, and begins to feel pain.

In such a serious case, the resin denture base molded by using a methyl methacrylate resin (acrylic resin) that is usually used is not sufficient for stably maintaining the mastication and supporting the adhesion of the denture. That is, it is necessary to reline the mucosa surface of the resin denture base with a soft dental relining material to compensate for the lost viscoelasticity of the mucosa of the residual alveolar ridge, in order to impart cushioning property that softens the occlusal stress. That is, the object of relining with a soft material is to overcome various troubles when the thin mucosa is compressed by the hard denture base.

Examples of relatively excellent soft relining materials include room temperature-curing silicone rubbers that are cured at room temperature of not higher than 50° C. and low temperature-curing silicone rubbers that cure at temperatures of from about 50° to about 150° C.

However, the silicone rubber-type relining materials are defective with respect to adhesiveness to the denture base. Therefore, several adhesives have heretofore been developed for adhering a silicone rubber material which is the relining material to an acrylic resin which is the denture base. For instance, there have been developed a silicone-modified acrylic resin using a copolymer of an alkyl (meth)acrylate and a dimethyl vinyl silylalkyl ester of (methy)acrylic acid (Japanese Laid-Open Patent Publication No. 43209/1990) and a silicone-modified acrylic resin using a copolymer of an alkyl (meth)acrylate and a dimethyl hydrogen silylalkyl ester of (meth)acrylic acid (Japanese Laid-Open Patent Publication No. 68007/1992).

That is, solutions in which the above resins are dissolved are applied onto the denture base and after drying, a room temperature-curing (hydrosilation reaction-curing) silicone paste which is a soft dental relining material is thickly applied thereon and is adhered being heated at about 80° C. during the curing and/or after the curing.

Using the above-mentioned conventional adhesives, however, the adhesiveness is still not satisfactory between the acrylic resin which is the denture base and the silicone rubber relining material. That is, using both above-mentioned adhesives, sufficient degree of adhesion is not obtained unless they are heated at about 80° C. for 20 to 30 minutes or longer.

SUMMARY OF THE INVENTION

It is therefore an object of the present invention to provide an adhesive which exhibits excellent adhesiveness and, particularly, which firmly adheres an acrylic resin and a silicone rubber at a temperature of as low as about 20° to 30° C. requiring a period of several minutes.

In order to solve the above-mentioned problems inherent in the prior art, the present inventors have conducted keen study and have found the fact that the acrylic resin and the silicone rubber could be firmly adhered together at a temperature of as low as about 20° to 30° C. by using a novel silicone-modified acrylic copolymer having a polyorganosiloxane with an SiH group on a side chain thereof, and have accomplished the present invention.

According to the present invention, there is provided a silicone-modified acrylic copolymer comprising:

I. a structural unit of the formula

wherein $R^1$ is a hydrogen atom, a methyl group or an ethyl group, and $R^3$ is an alkyl group with up to 13 carbon atoms or an aryl group with 6 to 14 carbon atoms, II. a structural unit of the formula

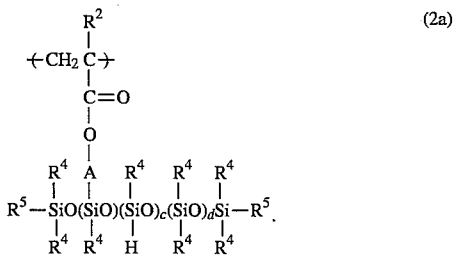

or of the formula

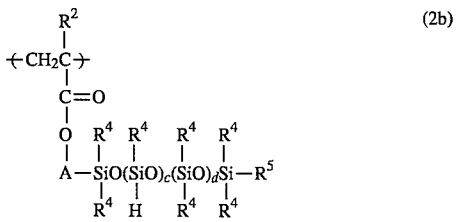

wherein $R^2$ is a hydrogen atom, a methyl group or an ethyl group, each of $R^4$ is an alkyl group with up to 6 carbon atoms or an aryl group with 6 to 14 carbon atoms which may the same or different, each of $R^5$ is a hydrogen atom, an alkyl group with up to 6 carbon atoms or an aryl group with 6 to 14 carbon atoms which may be the same or different, A is a divalent organic group with 2 to 20 carbon atoms which may have an ether bond or an ester bond in the main chain, and c and d are average recurring unit numbers, c being a number of 1 to 100 and d being a number of 0 to 100, and III. a structural unit of the formula

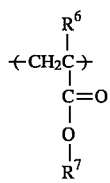  (3)

wherein $R^6$ is a hydrogen atom, a methyl group or an ethyl group, and $R^7$ is an ethylenically unsaturated hydrocarbon group with 2 to 20 carbon atoms which may have an ether bond or an ester bond in the main chain, wherein the unit (I), the unit (II) and the unit (III) are contained at ratios in mole % of (I)=10 to 99.9, (II)=90 to 0.1, and (III)=0 to 89.9, and have weight average molecular weights of from 5,000 to 1,000,000.

According to the present invention, there is further provided an adhesive comprising a solution obtained by dissolving the above-mentioned silicone-modified acrylic copolymer in a solvent therefor.

DETAILED DESCRIPTION OF THE PREFERRED EMBODIMENTS

Figure 1:
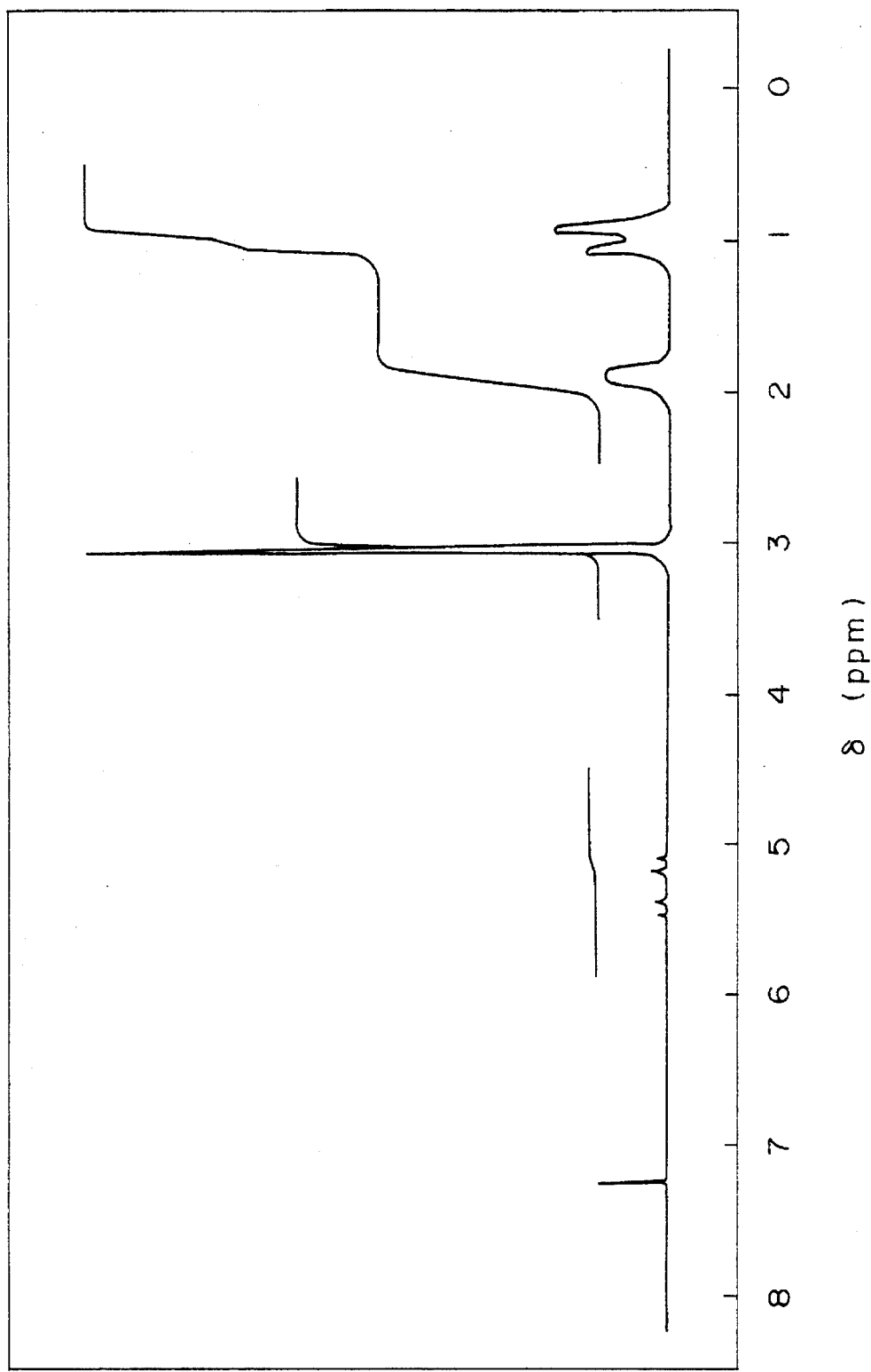
FIG. 1 is a diagram of magnetic resonance spectra ($^1$H-NMR spectra) of a polymethacrylate copolymer before being modified with silicone used in Example 1.

In the general formulas (1), (2a), (2b) and (3), $R^1$, $R^2$ and $R^6$ are selected from a hydrogen atom, a methyl group and an ethyl group. It is desired to use a mixture system in which $R^1$, $R^2$ and $R^6$ are hydrogen atoms, methyl groups or a combination thereof from the standpoint of easily obtaining the starting materials, easily synthesizing the copolymer and copolymerization reaction of the starting monomer (acrylate compound).

$R^3$ is selected from the alkyl groups with 1 to 13 carbon atoms such as a methyl group, an ethyl group, an n-propyl group, an n-hexyl group, a cyclohexyl group, an n-octyl group and a tridecyl group, as well as from the aryl groups with 6 to 14 carbon atoms such as a phenyl group, a benzyl group and a naphthyl group. Among them, lower alkyl groups such as a methyl group, an ethyl group and an n-propyl group are best suited, and a mixture system using one or two or more groups selected therefrom is desired.

$R^4$ is selected from the alkyl group with 1 to 6 carbon atoms such as a methyl group, an ethyl group, an n-propyl group and an n-hexyl group and from the aryl groups with 6 to 14 carbon atoms such as a phenyl group, a benzyl group and a naphthyl group. A methyl group, a phenyl group, or a mixture system thereof is desired from the standpoint of synthesizing and obtaining a polyorganosiloxane having an SiH group which is a synthesized starting material.

$R^5$ is a hydrogen atom, an alkyl group with 1 to 6 carbon atoms or an aryl group with 6 to 14 carbon atoms, which may be the same as that of $R^4$. A hydrogen atom, a methyl group, a phenyl group, or a mixture system thereof is desired from the standpoint of synthesizing and obtaining an organopolysiloxane having an SiH group which is a synthesized starting material and reactivity of the obtained copolymer.

$R^7$ is an ethylenically unsaturated hydrocarbon group with 2 to 20 carbon atoms which may have an ether bond or an ester bond in the main chain, such as a vinyl group, an allyl group, a 1-butenyl group, a 9-decenyl group, a 2-(2-(2-(2-propenyloxy)ethoxy)ethoxy) ethyl group, a 2-(3-butenoyloxy) ethyl group or an oleyl group.

A is a divalent hydrocarbon group with 2 to 20 carbon atoms which may have an ether bond or an ester bond in the main chain. A divalent hydrocarbon group with 3 to 10 carbon atoms which may have an ether bond or an ester bond is desired from the standpoint of easy synthesis. Described below are concrete examples of hydrocarbon groups.

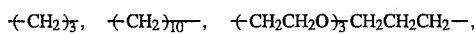

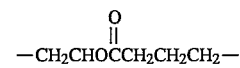

In the general formulas (2a) and (2b), c and d are average recurring unit numbers of the siloxane unit and are selected from integers that satisfy $1 \leq c \leq 100$ and $0 \leq d \leq 100$. From the standpoint of properties of the copolymer of the invention and easiness in the synthesis, it is desired to select c and d from ranges of $10 \leq c+d \leq 100$ and $0 \leq d/c \leq 10$. From the standpoint of reactivity of the adhesive, it is desired to so select c that a unit of polyorganosyloxane group has SiH groups in a number of three or more.

Copolymerization ratios of the structural units (1), structural units (2) and structural units (3) are so selected in mole % that (1)=10 to 99.9 mole %, (2)=90 to 0.1 mole %, and (3)=0 to 89.9 mole %. Desirably, the copolymerization ratios are so selected that (1)=50 to 99.9 mole %, (2)=50 to 0.1 mole %, and (3)=0 to 49.9 mole %. As far as the structural units are used within ranges represented by the above general formula, each structural unit may not be limited to a single kind of unit but may be constituted by a plurality of units.

When the ratio of the structural units (1) is smaller than 10 mole % with respect to the whole amount, and the ratio of the remaining structural units (2a) or (2b) is large, the ratio of the polyorganosiloxane moiety in the whole copolymer becomes great as compared with the acrylic resin moiety despite the molecular weight of the polyorganosiloxane group is decreased, and the copolymer poorly fits to the acrylic resin which is the denture base, resulting in a drop in the adhesive force. When the ratio of the structural units (3) is large, furthermore, the unsaturated bond that exists in excess amounts impairs the curing reaction of the room temperature-curing (hydrosilation reaction-curing) silicone to which the resin is to be adhered, and the adhesive rails to act to a sufficient degree. When the ratio of the structural units (2a) or (2b) is 0.1 mole % or smaller, the ratio of the polyorganosiloxane moiety becomes small in the whole copolymer, and the copolymer poorly fits to the silicone rubber which is the relining material, and the adhesive force to the silicone rubber becomes insufficient. Here, the polyorganosiloxane moiety stands for an SiO skeltal moiety having an organic group, which is a moiety determined by $R^4$, $R^5$, c and d. Furthermore, the acrylic resin moiety stands for a polyacrylate skeltal moiety other than the polyorganosiloxane moiety of the copolymer of the present invention, i.e., stands for a moiety determined by $R^1$ to $R^3$, $R^6$, $R^7$, and the numbers of the structural units (1), structural units (2a) or (2b) and structural units (3).

The copolymer of the present invention has a weight average molecular weight of from 5,000 to 1,000,000, and c, d and copolymerization ratios of the structural units (1), structural units (2a) or (2b) and structural units (3), and their total polymerization number are determined such that the above-mentioned range is accomplished.

It is further desired that the ratio of the molecular weight of the polyorganosiloxane moiety to the molecular weight of the acrylic resin moiety is 1:0.1 to 2 from the standpoint of compatibility and reactivity of the acrylic resin and the silicone rubber moiety and easiness of synthesis.

In the silicone-modified acrylic copolymer of the present invention, it is desired that $R^1$, $R^2$ and $R^6$ in the structural units represented by the above general formulas (1), (2) and (3) are selected from hydrogen atoms or methyl groups, $R^3$ is an alkyl group with up to 13 carbon atoms such as a methyl group or an ethyl group, $R^4$ is a methyl group or a phenyl group, $R^5$ is a hydrogen atom, a methyl group or a phenyl group, $R^7$ is an alkenyl group with 3 to 10 carbon atoms, A is a divalent alkylene group with 3 to 10 carbon atoms such as a propylene group, a butylene group or a decylene group, c and d are integers of $1 \leq c \leq 100$ and $0 \leq d \leq 100$ which are so selected that $10 \leq c+d \leq 100$ and $0 \leq d/c \leq 10$, the ratios of the structural units (1), structural units (2) and structural units (3) are (1)=50 to 99.9 mole %, (2)=50 to 0.1 mole %, (3)=0 to 49.9 mole %, and their weight average molecular weights are from 5,000 to 1,000,000, from the standpoint of easily obtaining the synthesized starting material, easiness of synthesis, and firmly adhering property stemming from the excellent reactivity of the obtained copolymer.

Concretely described below are structures of the structural units and average recurring unit numbers of representative examples of the silicone-modified acrylic copolymer of the present invention.

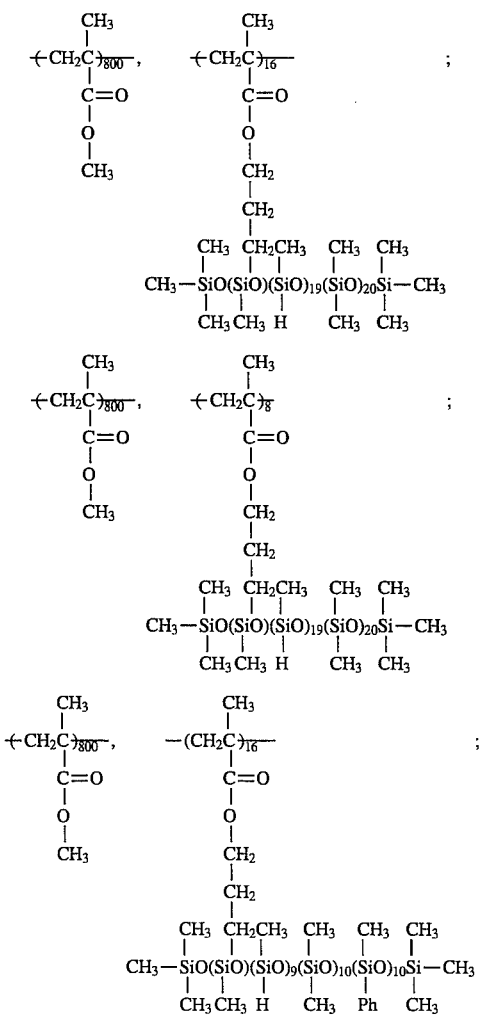

$$-(CH_2C)_{300}-, \quad -(CH_2C)_{20}-$$
(with H, C=O, O, CH₃ on first; H, C=O, O, CH₂, CH₂, and siloxane chain CH₃—SiO(SiO)(SiO)₁₉Si—CH₃ with CH₃CH₃, CH₂CH₃/H, CH₃ substituents on second);

$$-(CH_2C)_{450}-, \quad -(CH_2C)_{15}-$$
(CH₃; C=O, O, C₃H₇ / CH₃; C=O, O, CH₂, CH₂, Ph—SiO(SiO)(SiO)₁₉(SiO)₁₀Si—Ph with CH₃CH₃, CH₂CH₃/H, CH₃, CH₃);

$$-(CH_2C)_{700}-, \quad -(CH_2C)_{35}-$$
(CH₃; C=O, O, CH₃ / CH₃; C=O, O, CH₂, CH₂, H—SiO(SiO)(SiO)₄(SiO)₅Si—H, CH₃CH₃, CH₂CH₃/H, CH₃, CH₃);

$$-(CH_2C)_{500}-, \quad -(CH_2C)_{10}-$$
(CH₃; C=O, O, CH₃ / CH₃; C=O, O, CH₂, CH₂, Ph—SiO(SiO)(SiO)₁₉(SiO)₂₀Si—Ph, CH₃CH₃, CH₂CH₃/H, CH₃, CH₃);

$$-(CH_2C)_{500}-, \quad -(CH_2C)_{10}-$$
(CH₃; C=O, O, CH₃ / CH₃; C=O, O, CH₂, CH₂, O, CH₂, CH₂, CH₃—SiO(SiO)(SiO)₁₉(SiO)₂₀Si—CH₃, CH₃CH₃, CH₂CH₃/H, CH₃, CH₃);

$$-(CH_2C)_{2000}-, \quad -(CH_2C)_{50}-$$
(CH₃; C=O, O, CH₃ / CH₃; C=O, O, CH₂, CH₂, H—SiO(SiO)(SiO)₉(SiO)₁₀(SiO)₁₀Si—H, CH₃CH₃, CH₂CH₃/H, CH₃, C₃H₇, CH₃);

$$-(CH_2C)_{300}-, \quad -(CH_2C)_{20}-$$
(CH₃; C=O, O, CH₃ / CH₃; C=O, O, CH₂, CH₂, Ph—SiO(SiO)(SiO)₅Si—Ph, CH₃CH₃, CH₂CH₃/H, CH₃);

$$-(CH_2C)_{800}-, \quad -(CH_2C)_{10}-$$
(CH₃; C=O, O, CH₃ / CH₃; C=O, O, CH₂, CH₂, CH₃—SiO(SiO)(SiO)₁₉(SiO)₂₀Si—CH₃, CH₃CH₃, CH₂CH₃/H, CH₃, CH₃);

$$-(CH_2C)_{10}-$$
(CH₃; C=O, O, CH₂CH=CH₂);

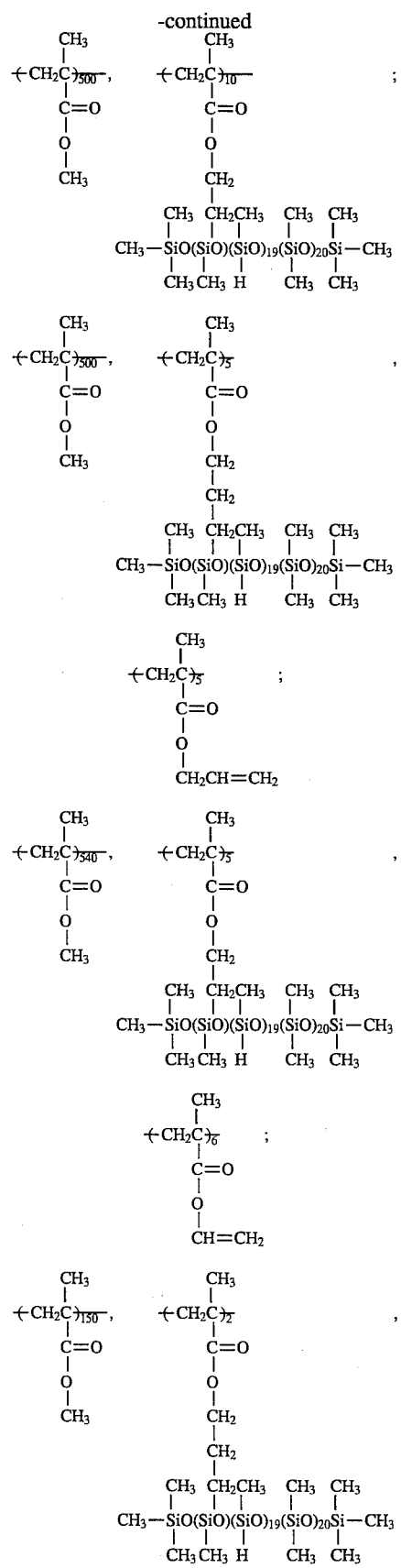
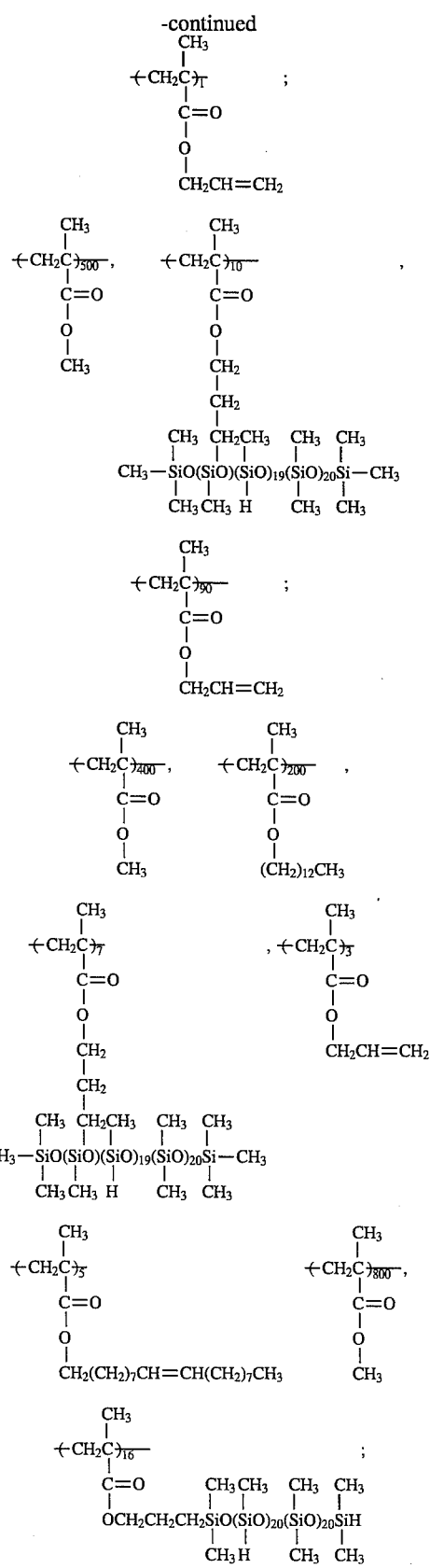

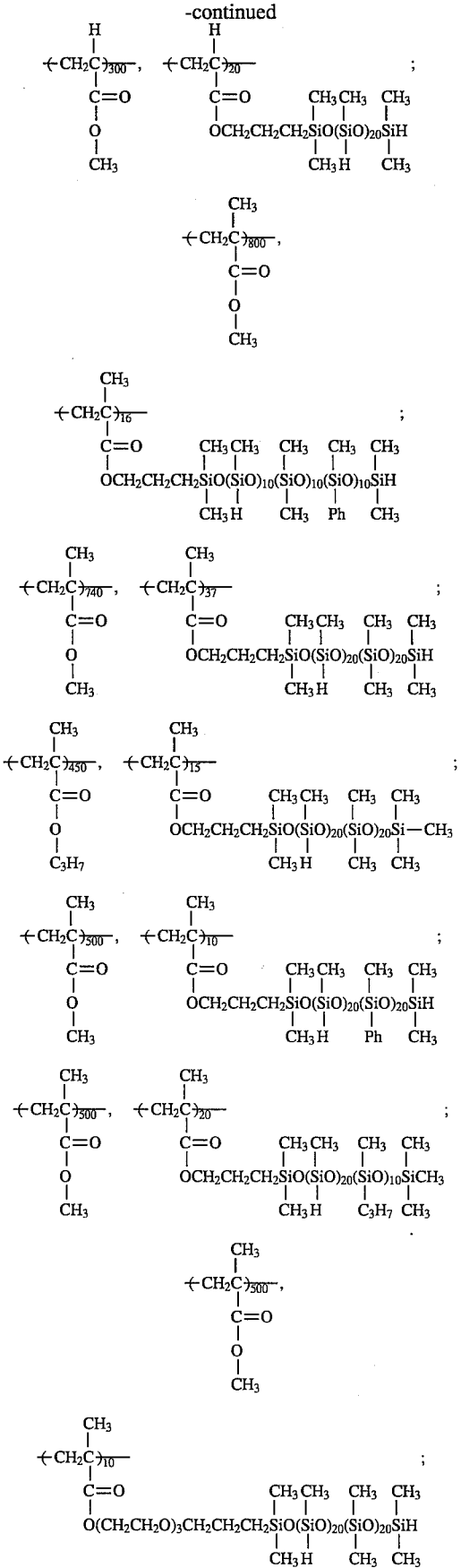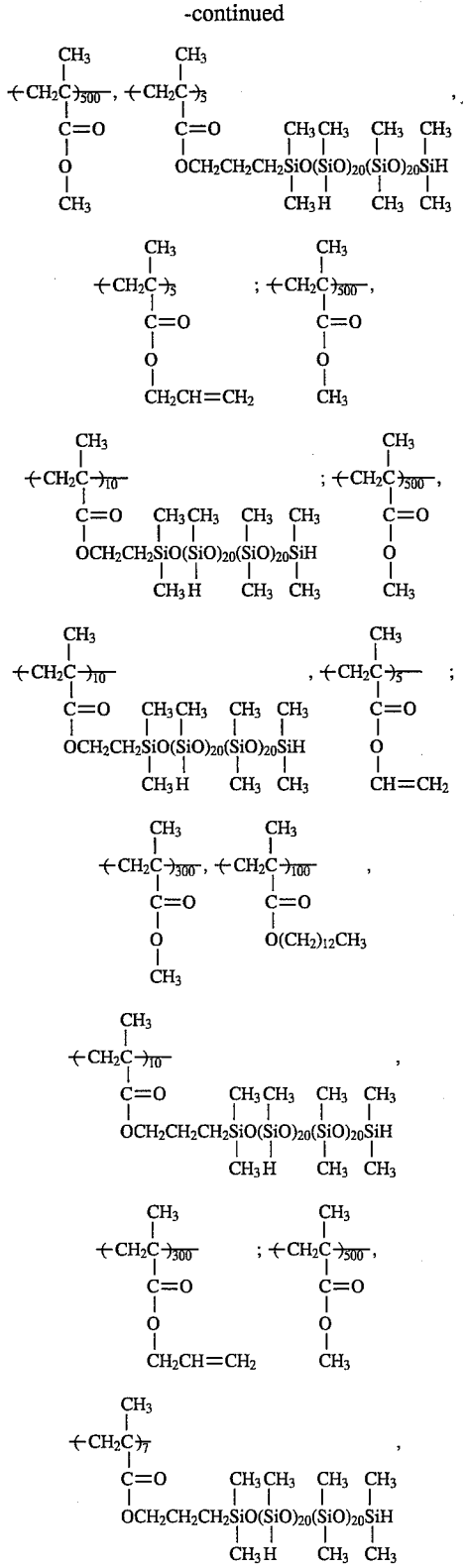

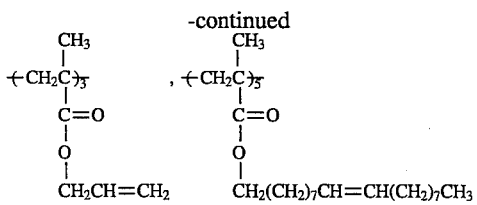

(wherein Ph denotes a phenyl group). In the copolymer of the present invention that will be used in Examples and Comparative Examples described later, the structural units and the order of bonds of siloxane units in the polyorganosiloxane moiety are quite arbitrary, and the recurring unit numbers appearing in the structural formula simply represent the structural units and average total weights of the siloxane units.

There is no particular limitation in the method of producing the silicone-modified acrylic copolymer of the present invention. A representative method, however, will be described hereinbelow.

The silicone-modified acrylic copolymer is produced by adding a hydrogen silicone compound represented by the general formula (7a) or (7b)

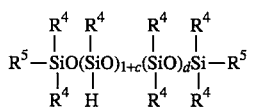

wherein $R^4$, $R^5$, c and d are as defined in the general Formula (2a), or

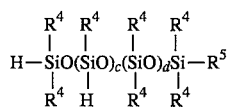

wherein $R^4$, $R^5$, c and d are as defined in the general formula (2b) to a copolymer of an acrylate compound represented by the general formula (4)

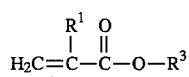

wherein $R^1$ and $R^3$ are as defined in the general formula (1), a terminal unsaturated bond-containing acrylate compound represented by the general formula (5)

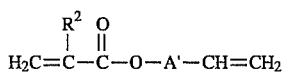

wherein $R^2$ is as defined in the general formula (2), and A' is a single bond, i.e., directly bonded an oxygen atom on the left of A' and a carbon atom on the right, or a divalent hydrocarbon group with 1 to 18 carbon atoms which may have an ether bond or an ester bond on the main chain, and, as required, an ethylenically unsaturated bond-containing acrylate compound represented by the general formula (6)

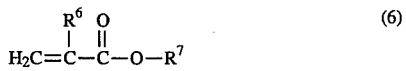

wherein $R^6$ and $R^7$ are as defined in the general formula (3), by the hydrosilation reaction using a platinum catalyst.

According to the above-mentioned synthesizing method, when the ethylenically unsaturated bond-containing acrylate compound of the general formula (6) is not used, $R^7$ in the structural unit (3) becomes the unreacted residue in the terminal unsaturated bond-containing acrylate compound of the general formula (5) which is the synthesized starting material, i.e., becomes —A'—CH=CH$_2$. When the ethylenically unsaturated bond-containing acrylate compound of the general formula (6) is used, $R^7$ in the structural units (3) becomes $R^7$ of the ethylenically unsaturated bond-containing acrylate compound of the general formula (6) or a mixture of $R^7$ of the ethylenically unsaturated bond-containing acrylate compound of the general formula (6) and the unreacted residue of the terminal unsaturated bond-containing acrylate compound of the general formula (5).

Synthesis thereof, i.e., copolymerization reaction of the acrylate compound, terminal unsaturated bond-containing acrylate compound and, as required, ethylenically unsaturated bond-containing acrylate compound, and the hydrosilation reaction of the copolymer and the hydrogen silicone compound, can all be carried out according to conventional methods.

The copolymer is synthesized, for example, as described below. That is, the acrylate compound, terminal unsaturated bond-containing acrylate compound and, as required, ethylenically unsaturated bond-containing acrylate compound as well as a radical polymerization initiator such as benzoyl peroxide or azobisisobutylonitrile are solution polymerization, i.e., are heated and polymerized in a solvent such as toluene, methylene chloride or chloroform, or are suspension polymerization by being polymerized in the water using a surfactant.

The hydrosilation reaction is carried out as described below. That is, an acrylic polymer having a double bond at a terminal of the side chain, a hydrogen silicone compound of an excess molar amount with respect to the amount of the terminal double bonds of the acrylic polymer that has double bonds at the terminal of the side chain, an inert solvent such as toluene or methylene chloride that simultaneously dissolves the hydrogen silicone compound and the acrylic polymer having double bond at the terminal of the side chain, and a platinum catalyst are fed into a reaction vessel, and are heated with stirring while bubbling nitrogen or the like gas to remove the effect of water, thereby to obtain the silicone-modified acrylic copolymer of the present invention.

The copolymer of the present invention can be further obtained even by copolymerizing a hydrogen silicone compound having a (meth)acryloxyalkyl group on the side chain, the acrylate compound of the above general formula (4) and, as required, the acrylate compound of the general formula (6).

As will be obvious from the above-mentioned synthesizing methods, it is quite free to select the resin constituent elements such as the whole molecular weight of the silicone-modified acrylic copolymer of the present invention, molecular weight of the polyacrylate moiety, copolymerization ratios of the structural units (1), structural units (2a) or (2b) and structural units (3), molecular weight of the polyorganosiloxane moiety, ratio of the each siloxane units (c/d), organic groups $R^1$ to $R^7$, kind of A, and combinations thereof.

That is, the molecular weight of the polyacrylate moiety can be controlled by a conventional method such as adjusting the amount of the polymerization initiating catalyst at the time of copolymerization reaction and by adding a chain transfer agent. The copolymerization ratios of the structural units (1), structural units (2a) or (2b) and structural units (3) can be controlled by controlling the feeding ratio of the corresponding monomers and controlling the conversion of the addition reaction of the hydrogen silicone compound, i.e., by controlling the reaction conditions, or by using the monomers having organic groups $R^1$ to $R^7$ and A at predetermined mixing ratios and controlling the conversion of the adding reaction of the hydrogen silicone compound, i.e., controlling the reaction conditions. As for the polyorganosiloxane moiety, the molecular weight, ratio of each of the siloxane units (c/d), kinds of the organic groups $R^4$ and $R^5$, and combinations thereof, can be artitrarily controlled.

The thus obtained silicone-modified acrylic copolymer is generally in the form of a white powdery solid material.

The silicone-modified acrylic copolymer is quite a novel compound and exhibits astonishing properties when it is used as an adhesive.

To use the silicone-modified acrylic copolymer as an adhesive, the copolymer is dissolved in an organic solvent such as toluene, methylene chloride, chloroform or tetrahydrofurane at a suitable concentration and, preferably, at a concentration of from about 0.1 to about 20% by weight. A preferred example of the solvent is a highly volatile methylene chloride or toluene.

A typical use of the adhesive is as described below. That is, the adhesive is applied to the denture base, the solvent is allowed to evaporate, a hydrosilation reaction-curing silicone paste which is a soft dental relining material is thickly applied thereon and is cured. The adhesive adheres to the acrylic resin as the hydrosilation reaction-curing silicone paste cures, and the adhesion is completed by the time when the silicone paste is cured.

The mechanism in which a firm adhesion is accomplished within such short periods of time is not yet sufficiently clarified but is presumed to be as described below.

That is, the organic solvent dissolving the copolymer of the present invention swells the acrylic resin into which the polyacrylate moiety of the copolymer of the present invention permeates, causing the polyacrylate chains to be molecularly intermingled. On the other hand, the polyorganosiloxane moiety having an SiH group floats on the surface of the adhesive layer. When the hydrosilation reaction-curing silicone paste is applied thereon, they fit to each other very well since they are the same organopolysiloxane and, besides, a double bond in the silicone paste reacts with the SiH group of the polysiloxane moiety in the adhesive resin of the present invention. It is thus considered that the acrylic resin and the adhesive layer firmly adhere to each other, and the adhesive layer and the cured product of silicone rubber firmly adhere to each other.

The adhesive using the silicone-modified acrylic copolymer of the present invention exhibits superior adhesiveness to the adhesives disclosed in Japanese Laid-Open Patent Publication No. 43209/1990 and Japanese Laid-Open Patent Publication No. 68007/1992. As for the polyacrylate moieties, three of them have a similar structure and a difference in the adhesiveness stems from a difference in the siloxane group. One of the reasons why the adhesive having the polyorganosiloxane structure of the present invention exhibits excellent adhesiveness is attributed to the fact that this structure fits well to the hydrosilation reactive silicone paste and reacts well with the hydrosilation reactive silicone paste.

That is, the silicone reactive moiety of the silicone-modified acrylic resin disclosed in Japanese Laid-Open Patent Publication No. 43209/1990 has a molecular structure

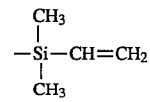

and the silicone reactive moiety of the silicone-modified acrylic resin disclosed in Japanese Laid-Open Patent Publication No. 68007/1992 has a molecular structure

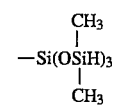

On the other hand, the silicone moiety of the copolymer of the present invention has a molecular structure

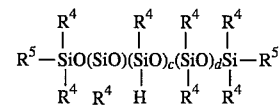

wherein $R^4$, $R^5$, c and d are as defined in the general formula (2a), or

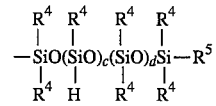

wherein $R^4$, $R^5$, c and d are as defined in the general formula (2b).

According to the structure of Japanese Laid-Open Patent Publication No. 43209/1990, the reactive group of the adhesive component is a double bond. In the curing reaction of the silicone paste in this case, it has been known from the mechanism of hydrosilation reaction that the reactivity increases with an increase in the amount of SiH in the whole reaction system. Even from this point, it is obvious that the reactivity on the interface of adhesion is inferior to other two kinds. When the molecular structure of the silicone-modified acrylic resin of Japanese Laid-Open Patent Publication NO. 68007/1992 is compared with the molecular structure of the copolymer of the present invention, the reactive group is SiH group in both of them. However, the polyorganosiloxane moiety has a large effective surface area in the molecular structure of the copolymer of the present invention causing the layer to be isolated in the polyorganosiloxane moiety polyacrylate moiety. With the layer being easily isolated, the reactive polyorganosiloxane tends to float on the surface of the adhesive layer when the adhesive is applied and is dried, contributing to improving fitness to the curable silicone paste and reactivity.

The adhesive agent using the novel silicone-modified acrylic copolymer of the present invention is capable of firmly adhering the acrylic resin and the silicone rubber together at a temperature of as low as from 20° to 30° C.

EXAMPLES

Described below are Working Examples for further concretely explaining the present invention which, however, is in no way limited to these Examples only.

Compounds used in the following adhesion tests and in Examples and Comparative Examples are shown in Table 1 and are abbreviated as shown in Table 1 (wherein Ph denotes a phenyl group).

TABLE 1

| Structure | Abbreviation |
|---|---|
| $H_2C=CH-\underset{\underset{CH_3}{\mid}}{\overset{\overset{CH_3}{\mid}}{Si}}O(\underset{\underset{CH_3}{\mid}}{\overset{\overset{CH_3}{\mid}}{Si}}O)_{500}\underset{\underset{CH_3}{\mid}}{\overset{\overset{CH_3}{\mid}}{Si}}-CH=CH_2$ | DVS-M500 |
| $CH_3-\underset{\underset{CH_3}{\mid}}{\overset{\overset{CH_3}{\mid}}{Si}}O(\underset{\underset{CH_3}{\mid}}{\overset{\overset{CH_3}{\mid}}{Si}}O)_{20}(\underset{\underset{H}{\mid}}{\overset{\overset{CH_3}{\mid}}{Si}}O)_{20}\underset{\underset{CH_3}{\mid}}{\overset{\overset{CH_3}{\mid}}{Si}}-CH_3$ | DMS-M20H20 |
| $CH_3-\underset{\underset{CH_3}{\mid}}{\overset{\overset{CH_3}{\mid}}{Si}}O(\underset{\underset{CH_3}{\mid}}{\overset{\overset{CH_3}{\mid}}{Si}}O)_{20}(\underset{\underset{H}{\mid}}{\overset{\overset{CH_3}{\mid}}{Si}}O)_{10}\underset{\underset{CH_3}{\mid}}{\overset{\overset{CH_3}{\mid}}{Si}}-CH_3$ | DMS-M20H10 |
| $CH_3-\underset{\underset{CH_3}{\mid}}{\overset{\overset{CH_3}{\mid}}{Si}}O(\underset{\underset{H}{\mid}}{\overset{\overset{CH_3}{\mid}}{Si}}O)_{20}\underset{\underset{CH_3}{\mid}}{\overset{\overset{CH_3}{\mid}}{Si}}-CH_3$ | DMS-H20 |
| $CH_3-\underset{\underset{CH_3}{\mid}}{\overset{\overset{CH_3}{\mid}}{Si}}O(\underset{\underset{CH_3}{\mid}}{\overset{\overset{CH_3}{\mid}}{Si}}O)_{10}(\underset{\underset{H}{\mid}}{\overset{\overset{CH_3}{\mid}}{Si}}O)_{10}(\underset{\underset{Ph}{\mid}}{\overset{\overset{CH_3}{\mid}}{Si}}O)_{10}\underset{\underset{CH_3}{\mid}}{\overset{\overset{CH_3}{\mid}}{Si}}-CH_3$ | DMS-M10H10P10 |
| $Ph-\underset{\underset{CH_3}{\mid}}{\overset{\overset{CH_3}{\mid}}{Si}}O(\underset{\underset{CH_3}{\mid}}{\overset{\overset{CH_3}{\mid}}{Si}}O)_{20}(\underset{\underset{H}{\mid}}{\overset{\overset{CH_3}{\mid}}{Si}}O)_{20}\underset{\underset{CH_3}{\mid}}{\overset{\overset{CH_3}{\mid}}{Si}}-Ph$ | DPS-P20H20 |
| $H-\underset{\underset{CH_3}{\mid}}{\overset{\overset{CH_3}{\mid}}{Si}}O(\underset{\underset{CH_3}{\mid}}{\overset{\overset{CH_3}{\mid}}{Si}}O)_{20}(\underset{\underset{H}{\mid}}{\overset{\overset{CH_3}{\mid}}{Si}}O)_{20}\underset{\underset{CH_3}{\mid}}{\overset{\overset{CH_3}{\mid}}{Si}}-H$ | DHS-M20H20 |
| $CH_3-\underset{\underset{CH_3}{\mid}}{\overset{\overset{CH_3}{\mid}}{Si}}O(\underset{\underset{CH_3}{\mid}}{\overset{\overset{CH_3}{\mid}}{Si}}O)_{20}(\underset{\underset{H}{\mid}}{\overset{\overset{CH_3}{\mid}}{Si}}O)_{20}\underset{\underset{CH_3}{\mid}}{\overset{\overset{CH_3}{\mid}}{Si}}-H$ | MHS-M20H20 |
| $H-\underset{\underset{CH_3}{\mid}}{\overset{\overset{CH_3}{\mid}}{Si}}O(\underset{\underset{CH_3}{\mid}}{\overset{\overset{CH_3}{\mid}}{Si}}O)_{10}(\underset{\underset{H}{\mid}}{\overset{\overset{CH_3}{\mid}}{Si}}O)_{10}(\underset{\underset{Ph}{\mid}}{\overset{\overset{CH_3}{\mid}}{Si}}O)_{10}\underset{\underset{CH_3}{\mid}}{\overset{\overset{CH_3}{\mid}}{Si}}-H$ | DHS-M10H10P10 |
| $H-\underset{\underset{CH_3}{\mid}}{\overset{\overset{CH_3}{\mid}}{Si}}O(\underset{\underset{Ph}{\mid}}{\overset{\overset{CH_3}{\mid}}{Si}}O)_{20}(\underset{\underset{H}{\mid}}{\overset{\overset{CH_3}{\mid}}{Si}}O)_{20}\underset{\underset{CH_3}{\mid}}{\overset{\overset{CH_3}{\mid}}{Si}}-H$ | DHS-P20H20 |
| $H-\underset{\underset{CH_3}{\mid}}{\overset{\overset{CH_3}{\mid}}{Si}}O(\underset{\underset{H}{\mid}}{\overset{\overset{CH_3}{\mid}}{Si}}O)_{20}\underset{\underset{CH_3}{\mid}}{\overset{\overset{CH_3}{\mid}}{Si}}-H$ | DHS-H20 |

The adhesion strength was measured as described below.
1) Test Materials

The following two kinds of pastes A and B were prepared as addition-type silicone rubbers. They were mixed together in the same amount and were cured to obtain a silicone rubber.

| | parts by weight |
|---|---|
| Paste A: | |
| DVS-M500 | 100 |
| particle of a polymethylsilsesquioxane (grain size, 2 μm) | 100 |
| Platinum/vinyl siloxane complex solution (platinum, 1000 ppm) | 1 |
| Paste B | |
| DVS-M500 | 97 |
| DMS-M20H20 | 3 |
| particle of a polymethylsilsesquioxane (grain size, 2 μm) | 100 |

The cured product of the silicone rubber prepared here exhibited a tensile strength of about 20 Kgf/cm².
1) Testing Method A solution of the prepared adhesive was applied onto an acrylic plate of which the surface had been polished with a water-resistant sand-paper #800 by pouring the water, and was dried for about one minute. The pastes A and B that were well mixed together in an equal amount were then thickly applied onto the acrylic plate to which the solution of the adhesive has been applied. The acrylic plate was placed under the adhesion conditions shown in Tables 4 and 5, taken out after a predetermined period of time had passed, and was evaluated concerning the adhering force.

3) Evaluation of Adhering Force

After a predetermined period of time had passed, it was attempted to peel them apart along the interface between the acrylic plate and the cured silicone rubber using a spatula, and the manner of destruction in this case was observed and evaluated. The evaluation relied upon the following points A to D.

A: Aggregation destruction of the whole silicone rubber (adhering force>20 Kgf/cm²).

B: Mixed destruction of aggregation destruction and interface destruction (adhering force was nearly 20 Kgf/cm²).

C: Interface destruction (adhering force<20 Kgf/cm²).

D: Interface destruction (not adhered at all) (adhering force is almost 0 Kgf/cm²).

Synthesis of the Silicone-Modified Acrylic Copolymers

Example 1

27.9 Grams of a DMS-M10H10P10, 300 ml of toluene and 0.33 g of a platinum/divinyl siloxane complex solution in which the amount of platinum had been adjusted to 1000 ppm were introduced into a flask, and were heated at 80° C. with stirring while bubbling nitrogen. A solution obtained by dissolving in 100 ml of toluene 5 g of a copolymer (weight average molecular weight, 102,000) of methyl methacrylate and allyl methacrylate at a copolymerization ratio of 50 to 1 (molar ratio), was dropwisely added thereto over a period of one hour. After the dropwise addition had been finished, the mixture was heated and stirred for 6 hours, toluene was removed under reduced pressure, an excess of DMS- M10H10P10 was washed with a methanol/ethanol mixture solvent, followed by filtration and drying to obtain 7.0 g of a silicone-modified acrylic copolymer (yield, 89.9%). The obtained polymer possessed a weight average molecular weight of 160,000 with the polystyrene as a standard. It was confirmed through the H-NMR spectra and ultimate analysis (C, H) that the obtained copolymer possessed the following structural units and the average recurring unit number.

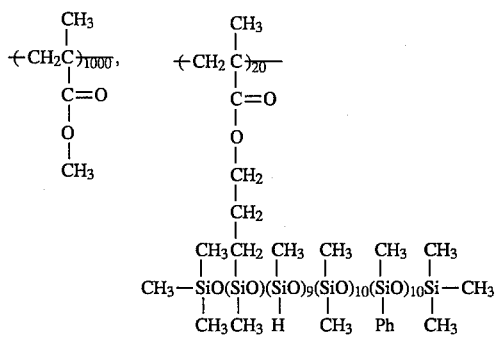

Figure 2:
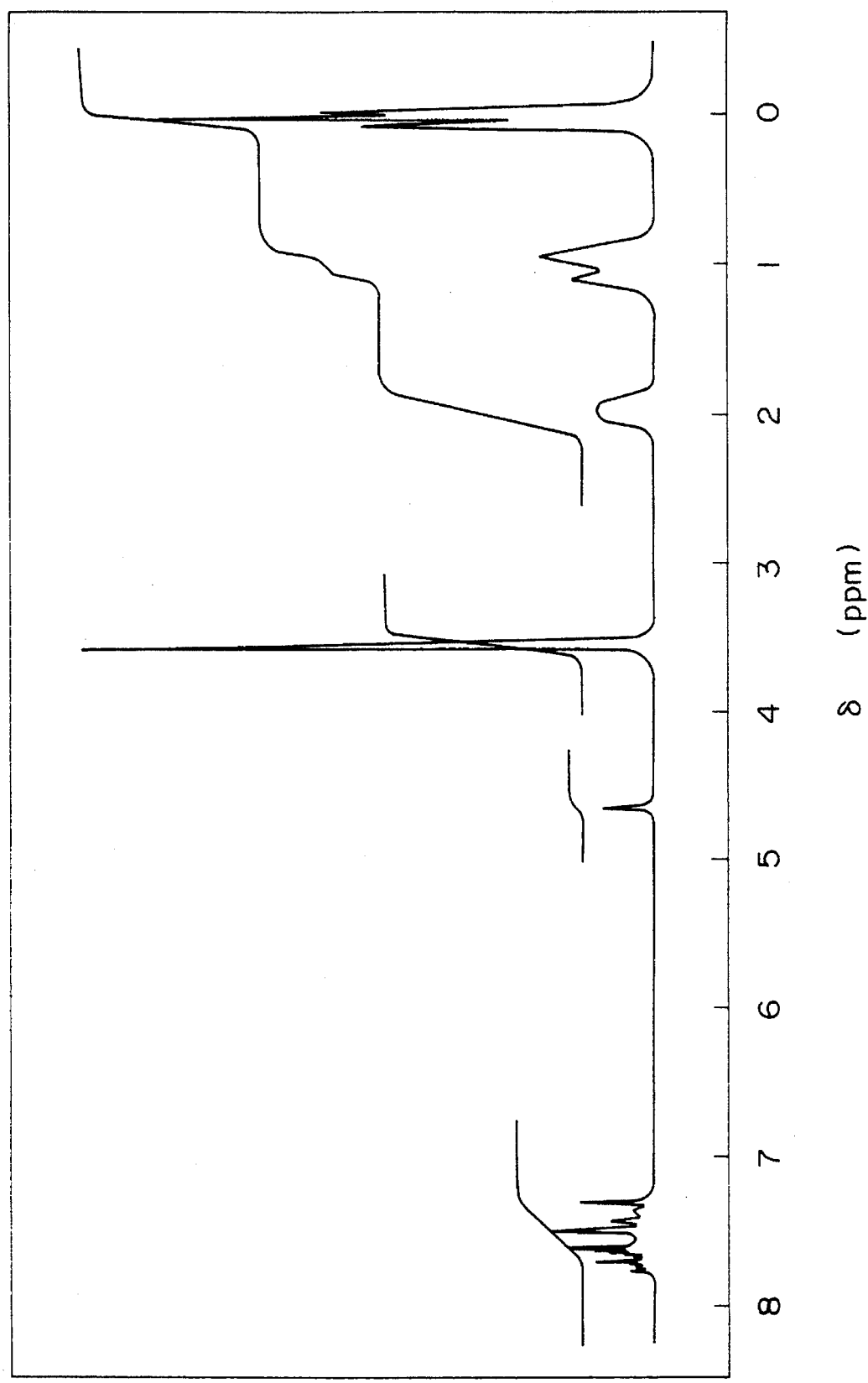
FIG. 2 is a diagram of magnetic resonance spectra ($^1$H-NMR spectra) of a silicone-modified acrylic copolymer obtained in Example 1.

(wherein Ph denotes a phenyl group). H/NMR spectra (CHCl$_3$ as a standard, δ ppm): FIG. 1 shows the spectra of a methacrylate polymer which is the synthesized starting material and FIG. 2 shows the spectra of the Formed product.

From the spectra (FIG. 1), broad peaks by the methacrylate polymer which is the synthesized starting material at 0.5 to 1.2 ppm and 1.5 to 2.2 ppm, a singlet peak by protons of the COO—CH$_3$ group at 3.5 ppm and multiplet peaks by protons of double bond of an allyl group at 5 to 6 ppm, whereas the spectra (FIG. 2) of the formed product exhibits no peak by the proton of the allyl group, but exhibits peak by protons of the SiH group at 4.6 ppm, peak by protons of the Si—CH$_3$ group at 0.1 ppm, and multipletpeaks by protons of Si—Ph (Ph is a phenyl group) group at 7 to 8 ppm. Moreover, the ratio of the strength of the singlet peak by protons of the COO—CH$_3$ group at 3.5 ppm to the strength of peak by protons of the Si—CH$_3$ group at 0.1 ppm (0.1 ppm/3.5 ppm, hereinafter abbreviated as S/PM) is 0.93 (S/PM=0.93 when they react quantitatively), from which it is learned that the addition reaction of the DMS-M10H10P10 to the allyl group is carried out nearly quantitatively.

Ultimate analysis (C, H): C 54.66%, H 7.69% were in good agreement with the calculated values C 54.53%, H 7.61%.

Example 2

14.0 Grams of a DMS-M20H20, 150 ml of toluene and 0.27 g of a platinum/divinyl siloxane complex solution in which the amount of platinum had been adjusted to 1000 ppm were introduced into a flask, and were heated at 80° C. with stirring while bubbling nitrogen. A solution obtained by dissolving in 100 ml of toluene 5 g of a copolymer (weight average molecular weight, 100,000) of methyl methacrylate and allyl methacrylate at a copolymerization ratio of 100 to 1 (molar ratio), was dropwisely added thereto over a period of one hour. The procedure was then carried out in the same manner as in Example 1 to obtain a silicone-modified acrylic copolymer. The obtained polymer possessed a weight average molecular weight of 127,000 with the polystyrene as a standard. It was confirmed through the H-NMR spectrum and ultimate analysis (C, H) that the obtained copolymer possessed the following structural units and the average recurring unit number

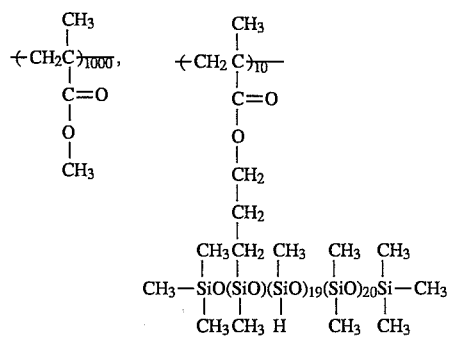

H-NMR spectra (CHCl$_3$ as a standard, δ ppm): Exhibited nearly the same spectra as those shown in Example 1. What made a difference was with regard to the presence and absence of the peak due to the phenyl group, and that area ratio of the peak due to the polysiloxane to the peak due to the polymethacrylate.

Ultimate analysis (C, H): C 53.06%, H 7.95% were in good agreement with the calculated values C 53.02%, H 7.93%.

Example 3

27.7 Grams of a DMS-M20H20, 300 ml of toluene and 0.33 g of a platinum/divinyl siloxane complex solution in which the amount of platinum had been adjusted to 1000 ppm were introduced into a flask, and were heated at 80° C. with stirring while bubbling nitrogen. A solution obtained by dissolving in 100 ml of toluene 5 g of a copolymer (weight average molecular weight, 102,000) of methyl methacrylate and allyl methacrylate at a copolymerization ratio of 50 to 1 (molar ratio), was dropwisely added thereto over a period of one hour. The procedure was then carried out in the same manner as in Example 1 to obtain a silicone-modified acrylic copolymer. The obtained polymer possessed a weight average molecular weight of 160,000 with the polystyrene as a standard. It was confirmed through the H-NMR spectrum and ultimate analysis (C, H) that the obtained copolymer possessed the following structural units and the average recurring unit number

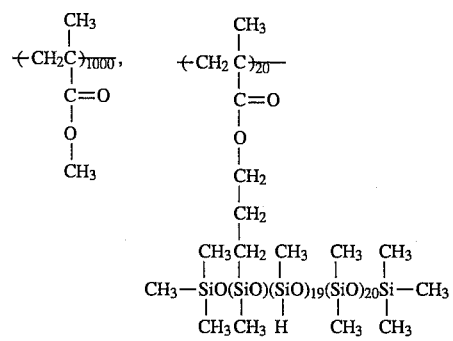

Figure 3:
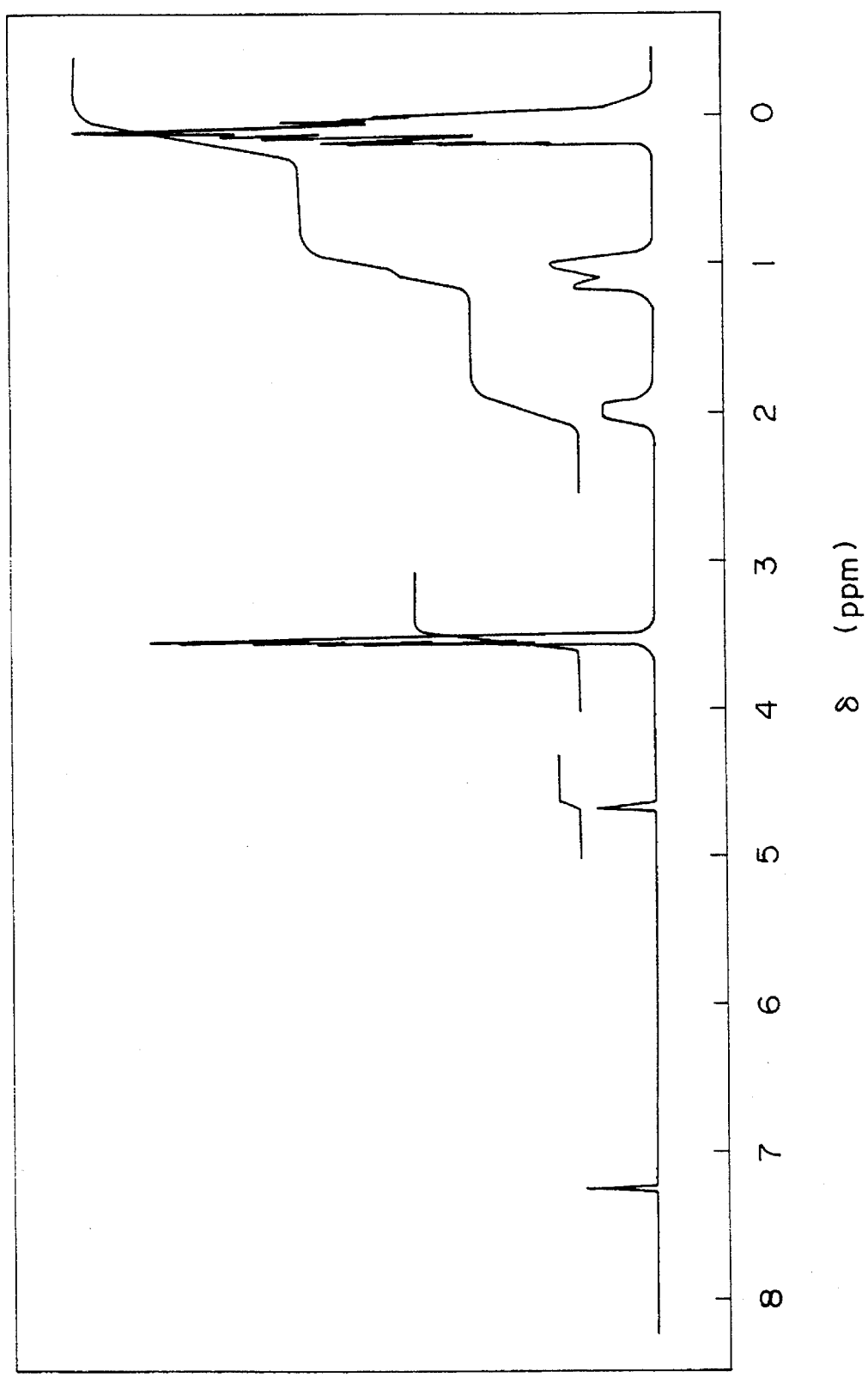
FIG. 3 is a diagram of magnetic resonance spectra ($^1$H-NMR spectra) of a silicone-modified acrylic copolymer obtained in Example 3.

H-NMR spectra (CHCl$_3$ as a standard, δ ppm): FIG. 3 shows the spectra of the formed product, from which it will be understood that the peak (5 to 6 ppm) by protons of the allyl group is extinguishing, and there are appearing peaks by protons of the SiH group at 4.6 ppm and by protons of the Si—CH$_3$ group at 0.1 ppm. The S/PM was 1.30 which was in good agreement with the calculated value (1.20).

Ultimate analysis (C, H): C 48.75%, H 7.95% were in good agreement with the calculated values C 48.64%, H 7.88%.

Example 4

41.9 Grams of a DMS-H20, 400 ml of toluene and 0.39 g of a platinum/divinyl siloxane complex solution in which the amount of platinum had been adjusted to 1000 ppm were introduced into a flask, and were heated at 80° C. with stirring while bubbling nitrogen. A solution obtained by dissolving in 100 ml of toluene 5 g of a copolymer (weight average molecular weight, 35,000) of methyl acrylate and allyl acrylate at a copolymerization ratio of 15 to 1 (molar ratio), was added dropwise thereto over a period of one hour. The procedure was then carried out in the same manner as in Example 1 to obtain a silicone-modified acrylic copolymer. The obtained polymer possessed a weight average molecular weight of 70,000 with the polystyrene as a standard. It was confirmed through the H-NMR spectrum and ultimate analysis (C, H) that the obtained copolymer possessed the following structural units and the average recurring unit number

Example 5

26.5 Grams of a DMS-M10H20, 250 ml of toluene and 0.33 g of a platinum/divinyl siloxane complex solution in which the amount of platinum had been adjusted to 1000 ppm were introduced into a flask, and were heated at 80° C. with stirring while bubbling nitrogen. A solution obtained by dissolving in 100 ml of toluene 5 g of a copolymer (weight average molecular weight, 75,000) of propyl methacrylate and allyl methacrylate at a copolymerization ratio of 30 to 1 (molar ratio), was added dropwise thereto over a period of one hour. The procedure was then carried out in the same manner as in Example 1 to obtain a silicone-modified acrylic copolymer. The obtained polymer possessed a weight average molecular weight of 113,000 with the polystyrene as a standard. It was confirmed through the H-NMR spectrum and ultimate analysis (C, H) that the obtained copolymer possessed the following structural units and the average recurring unit number

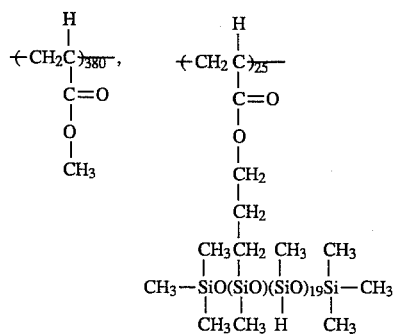

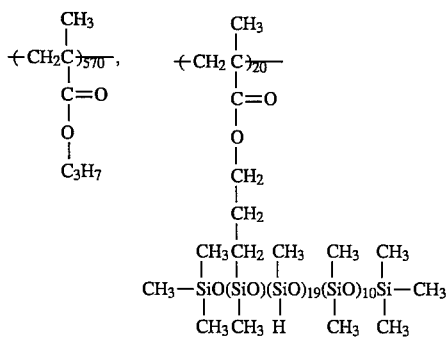

Example 6

13.4 Grams of a 1,1,3,3-tetramethyl disiloxane, 37.0 g of an octamethyl cyclotetrasiloxane, 16.0 g of a 1,3,5-trimethyl cyclotrisiloxane and 18.6 g of a hydrolyzed product of a 3-methacryloxypropylmethyl dimethoxysilane (chief component corresponds to a 1,3,5-tris(3-methacryloxypropyl)-1,3,5-trimethyl cyclotrisoloxane) were fed into a flask. The system was cooled at 5° C., and 0.4 g of a trifluoromethane sulfonic acid was added thereto. The system was then stirred at 5° to 10° C. for 12 hours, followed by washing with the water three times and distillation under a reduced pressure of about 10 mmHg at 50° to 60° C. to obtain a corresponding equilibrium product in an amount of 79.6 g (yield, 93.6%). Next, 250 g of a methyl methacrylate and 46.5 g of a methacrylic group-containing hydrogen silicone compound synthesized above were copolymerized (at a molar ratio of 50 to 1) by the solution polymerization method to obtain a silicone-modified acrylic copolymer. The obtained polymer possessed a weight average molecular weight of 125,000 with the polystyrene as a standard. It was confirmed through the H-NMR spectrum and ultimate analysis (C, H) that the obtained copolymer possessed the following structural units and the average recurring unit number

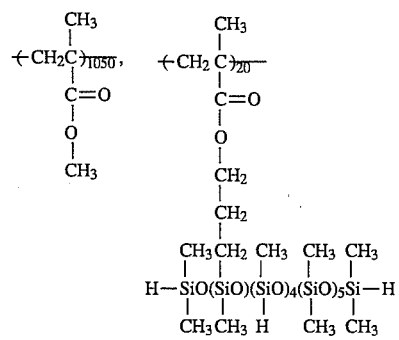

Example 7

29.5 Grams of a DPS-P20H20, 300 ml of toluene and 0.34 g of a platinum/divinyl siloxane complex solution in which the amount of platinum has been adjusted to 1000 ppm were introduced into a flask, and were heated at 80° C. with stirring while bubbling nitrogen. A solution obtained by dissolving in 100 ml of toluene 5 g of a copolymer (weight average molecular weight, 77,000) of methyl methacrylate and allyl methacrylate at a copolymerization ratio of 50 to 1 (molar ratio), was added dropwise thereto over a period of one hour. The procedure was then carried out in the same manner as in Example 1 to obtain a silicone-modified acrylic copolymer. The obtained polymer possessed a weight average molecular weight of 144,000 with the polystyrene as a standard. It was confirmed through the H-NMR spectrum and ultimate analysis (C, H) that the obtained copolymer possessed the following structural units and the average recurring unit number

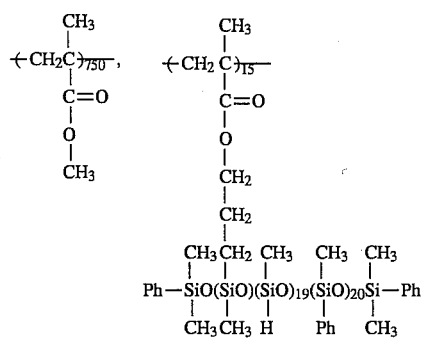

(wherein Ph is a phenyl group).

Example 8

27.0 Grams of a DMS-PM20H20, 300 ml of toluene and 033 g of a platinum/divinyl siloxane complex solution in which the amount of platinum had been adjusted to 1000 ppm were introduced into a flask, and were heated at 80° C. with stirring while bubbling nitrogen. A solution obtained by dissolving in 100 ml of toluene 5 g of a copolymer (weight average molecular weight, 63,000) of methyl methacrylate and triethylene glycol monoallyl ether ester of methacrylic acid at a copolymerization ratio of 50 to 1 (molar ratio), was added dropwise thereto over a period of one hour. The procedure was then carried out in the same manner as in Example 1 to obtain a silicone-modified acrylic copolymer. The obtained polymer possessed a weight average molecular weight of 95,000 with the polystyrene as a standard. It was confirmed through the H-NMR spectrum and ultimate analysis (C, H) that the obtained copolymer possessed the following structural units and the average recurring unit number

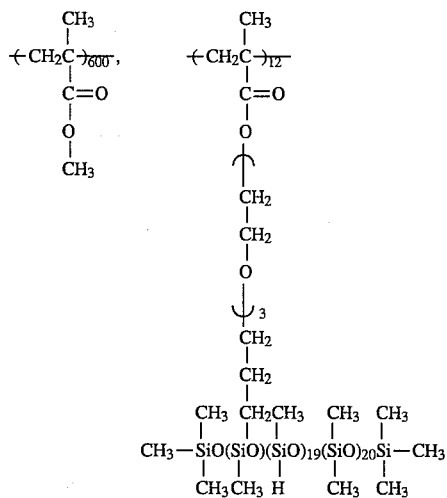

Example 9

5 Grams of a copolymer (weight average molecular weight, 52,000) of a methyl methacrylate and allyl methacrylate at a copolymerization ratio of 50 to 1 (molar ratio), 13.9 g of a DMB-M20H20, 150 ml of toluene, and 0.39 g of a platinum/divinyl siloxane complex solution in which the amount of platinum had been adjusted to 100 ppm were fed into a flask and were heated at 80° C. with stirring while bubbling nitrogen. After two hours had passed, the reaction was terminated, toluene was removed under reduced pressure, the excess of DMS-M20H20 was washed with hexane, followed by filtration and drying to obtain a silicone-modified acrylic copolymer in an amount of 6.2 g (yield, 79.7%). The obtained polymer possessed a weight average molecular weight of 66,000 with the polystyrene as a standard. It was confirmed through the H-NMR spectrum and ultimate analysis (C, H) that the obtained copolymer possessed the following structural units and the average recurring unit number

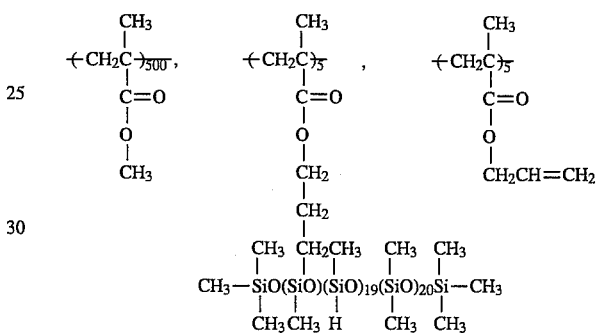

Figure 4:
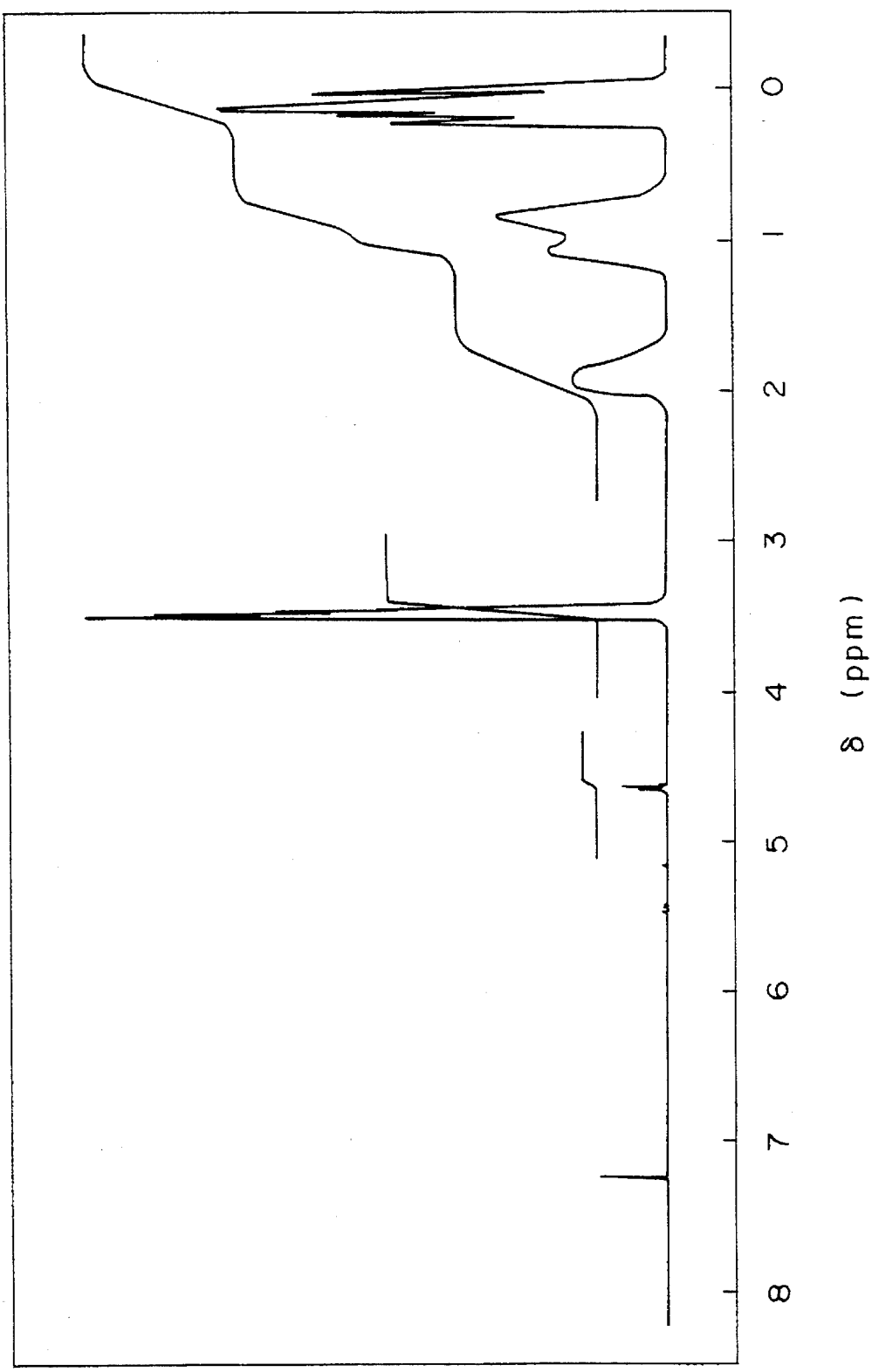
FIG. 4 is a diagram of magnetic resonance spectra ($^1$H-NMR spectra) of a silicone-modified acrylic copolymer obtained in Example 9.

H-NMR spectra (CHCl$_3$ as a standard, δ ppm): FIG. 4 shows the spectra of the formed product. The conversion of the DMS-M20H20 with respect to the allyl group was calculated from the ratio of the strength of singlet peak by protons of the COO—CH$_3$ group at 3.5 ppm of FIG. 4 to the strength of peak by protons of the Si—CH$_3$ group at 0.1 ppm (0.1 ppm/3.5 ppm=0.60) (0.1 ppm/3.5 ppm=1.20 when they react quantitatively) (conversion, 50.0%).

Ultimate analysis (C, H): C 53.10%, H 7.91% were in good agreement with the calculated values C 53.15%, H 7.93%.

Example 10

5 Grams of a copolymer (weight average molecular weight, 55,000) of a methyl methacrylate and vinyl methacrylate at a copolymerization ratio of 50 to 1 (molar ratio), 13.9 g of a DMS-M20H20, 150 ml of toluene, and 0.39 g of a platinum/divinyl siloxane complex solution in which the amount of platinum had been adjusted to 100 ppm were fed into a flask and were heated at 80° C. with stirring while bubbling nitrogen. After two hours had passed, the reaction was terminated, toluene was removed under reduced pressure, the excess of DMB-M20H20 was washed with hexane, followed by filtration and drying to obtain a silicone-modified acrylic copolymer in an amount of 6.1 g (yield, 78.4%). The obtained polymer possessed a weight average molecular weight of 69,000 with the polystyrene as a standard. It was confirmed through the H-NMR spectrum and ultimate analysis (C, H) that the obtained copolymer possessed the following structural units and the average recurring unit number

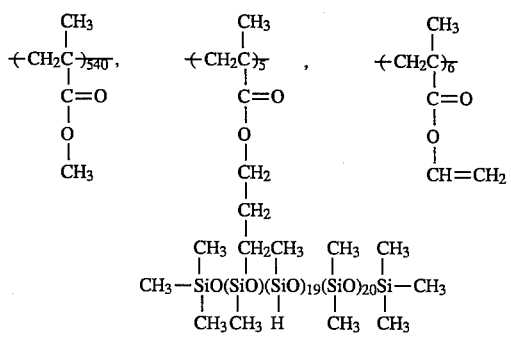

Example 11

5 Grams of a copolymer (weight average molecular weight, 15,000) of a methyl methacrylate and allyl methacrylate at a copolymerization ratio of 50 to 1 (molar ratio), 13.9 g of a DMS-M20H20, 150 ml of toluene, and 0.39 g of a platinum/divinyl siloxane complex solution in which the amount of platinum had been adjusted to 100 ppm were fed into a flask and were heated at 80° C. with stirring while bubbling nitrogen. After four hours have passed, the reaction was terminated, toluene was removed under reduced pressure, the excess of DMS-M20H20 was washed with hexane, followed by filtration and drying to obtain a silicone-modified acrylic copolymer in an amount of 5.8 g (yield, 74.7%). The obtained polymer possessed a weight average molecular weight of 20,000 with the polystyrene as a standard. It was confirmed through the H-NMR spectrum and ultimate analysis (C, H) that the obtained copolymer possessed the following structural units and the average recurring unit number

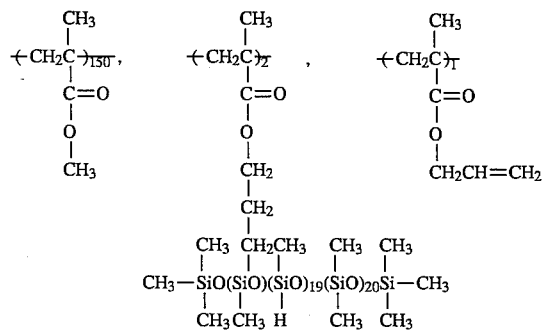

Example 12

5 Grams of a copolymer (weight average molecular weight, 63,000) of a methyl methacrylate and allyl methacrylate at a copolymerization ratio of 5 to 1 (molar ratio), 110 g of a DMS-M20H20, 1500 ml of toluene, and 0.39 g of a platinum/divinyl siloxane complex solution in which the amount of platinum had been adjusted to 100 ppm were fed into a flask and were heated at 60° C. with stirring while bubbling nitrogen. After two hours had passed, the reaction was terminated, toluene was removed under reduced pressure, the excess of DMS-M20H20 was washed with hexane, followed by filtration and drying to obtain a silicone-modified acrylic copolymer in an amount of 5.3 g (yield, 19.1%). The obtained polymer possessed a weight average molecular weight of 90,000 with the polystyrene as a standard. It was confirmed through the H-NMR spectrum and ultimate analysis (C, H) that the obtained copolymer possessed the following structural units and the average recurring unit number

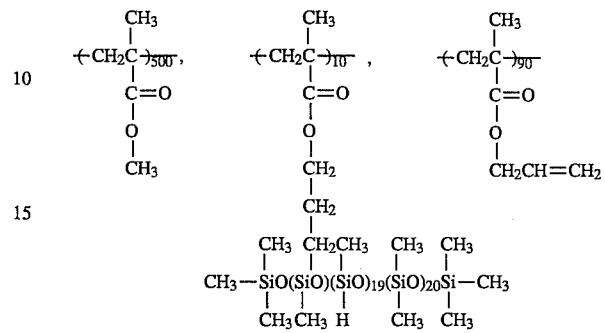

Example 13

5 Grams of a copolymer (weight average molecular weight, 67,000) of a methyl methacrylate, benzyl methacrylate and 9-decenyl methacrylate at a copolymerization ratio of 30 to 20 to 1 (molar ratio), 10.5 g of a DMS-M20H20, 100 ml of toluene, and 0.30 g of a platinum/divinyl siloxane complex solution in which the amount of platinum had been adjusted to 100 ppm were fed into a flask and were heated at 80° C. with stirring while bubbling nitrogen. After four hours had passed, the reaction was terminated, toluene was removed under reduced pressure, the excess of DMS-M20H20 was washed with hexane, followed by filtration and drying to obtain a silicone-modified acrylic copolymer in an amount of 6.0 g (yield, 84.5%). The obtained polymer possessed a weight average molecular weight of 84,000 with the polystyrene as a standard. It was confirmed through the H-NMR spectrum and ultimate analysis (C, H) that the obtained copolymer possessed the following structural units and the average recurring unit number

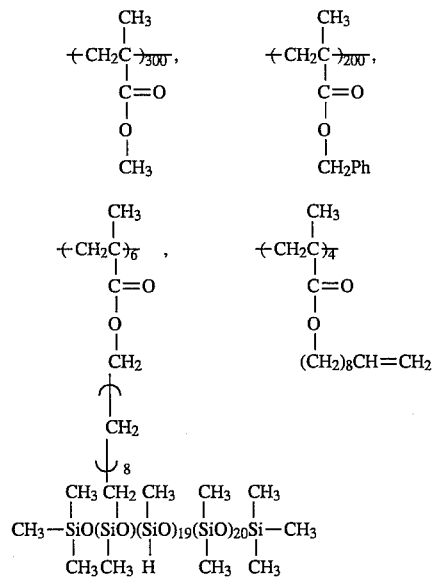

(wherein Ph is a phenyl group).

Example 14

5 Grams of a copolymer (weight average molecular weight, 70,000) of a methyl methacrylate, tridecyl methacrylate, allyl methacrylate and oleyl methacrylate at a copolymerization ratio of 400 to 10 to 1 to 0.5 (molar ratio), 10.2 g of a DMS-M20H20, 100 ml of toluene, and 0.30 g of a platinum/divinyl siloxane complex solution in which the amount of platinum had been adjusted to 100 ppm were fed into a flask and were heated at 80° C. with stirring while bubbling nitrogen. After four hours had passed, the reaction was terminated, toluene was removed under reduced pressure, the excess of DMS-M20H20 was washed with hexane, followed by filtration and drying to obtain a silicone-modified acrylic copolymer in an amount of 5.3 g (yield, 75.3%). The obtained polymer possessed a weight average molecular weight of 116,000 with the polystyrene as a standard. It was confirmed through the H-NMR spectrum and ultimate analysis (C, H) that the obtained copolymer possessed the following structural units and the average recurring unit number

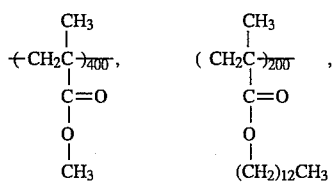

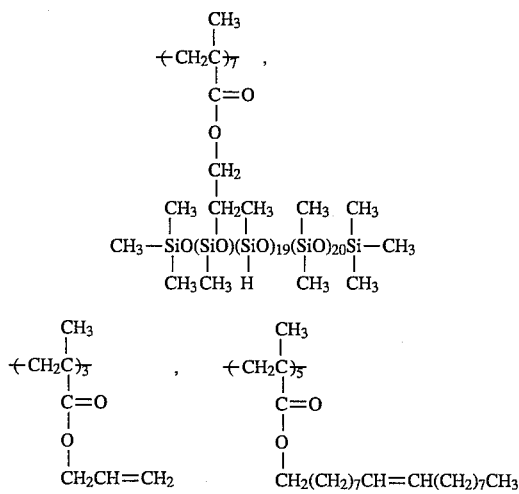

Weight average molecular weights and results of ultimate analysis of the silicone-modified acrylic copolymers synthesized in Examples 1 to 14 are shown in Table 2.

TABLE 2

| Example No. | Molecular weight (with polystyrene as standard) | Ultimate analysis (wt %)* | |
|---|---|---|---|
| | | C | H |
| 1 | 160000 | 54.66 (54.53) | 7.69 (7.61) |
| 2 | 127000 | 53.06 (53.02) | 7.95 (7.93) |
| 3 | 160000 | 48.75 (48.64) | 7.95 (7.88) |
| 4 | 70000 | 40.00 (40.04) | 7.12 (7.09) |
| 5 | 113000 | 53.01 (51.57) | 8.66 (8.68) |
| 6 | 125000 | 56.08 (56.02) | 8.02 (7.99) |
| 7 | 144000 | 55.79 (55.68) | 7.28 (7.20) |
| 8 | 95000 | 48.77 (48.81) | 7.99 (7.91) |
| 9 | 66000 | 53.10 (53.15) | 7.91 (7.93) |
| 10 | 69000 | 53.55 (53.50) | 7.95 (7.92) |
| 11 | 20000 | 52.40 (51.45) | 7.90 (7.91) |
| 12 | 90000 | 51.06 (50.89) | 7.92 (7.89) |
| 13 | 84000 | 60.13 (60.17) | 7.45 (7.51) |
| 14 | 116000 | 62.33 (62.27) | 9.85 (9.81) |

*calculated values are in parentheses.

Adhesives and Their Evaluation

Example 15

An adhesive was prepared by dissolving the copolymer synthesized in Example 1 in an amount of 0.5% by weight in the methylene chloride. By using a small brush, the adhesive was applied onto the acrylic plate and was dried for about one minute. The aforementioned addition-type silicone pastes A and B which are test materials were mixed well together in an equal amount, and were thickly applied onto the acrylic plate on which the adhesive solution has been applied. The acrylic plate was left to stand still in the water maintained at 32° C. for three minutes, and was taken out to evaluate the adhering force in compliance with the method of evaluation mentioned earlier. The result was A.

Examples 16 to 33

Adhesives of compositions shown in Table 3 were prepared by using silicone-modified acrylic copolymers synthesized in Examples 1 to 14 according to the preparation method of Example 15. These adhesives were evaluated for their adhesive force under the adhesion conditions shown in Table 3 in accordance with the above-mentioned method of evaluation. The results were as shown in Table 3.

TABLE 3

| Example No. | Adhesive polymer (synthesized in Examples 1–14) | Solvent | Concentration (wt %) | Adhesion condition (preserved in water) Temp. (°C.) | Time (min) | Evaluation |
|---|---|---|---|---|---|---|
| 15 | polymer of example 1 | methylene chloride | 0.5 | 32 | 3 | A |
| 16 | polymer of example 1 | methylene chloride | 10 | 32 | 3 | A |
| 17 | polymer of example 1 | toluene | 0.5 | 32 | 3 | A |
| 18 | polymer of example 2 | methylene chloride | 0.5 | 32 | 3 | A |
| 19 | polymer of example 3 | methylene chloride | 0.5 | 23 | 5 | A |
| 20 | polymer of example 4 | methylene chloride | 10 | 23 | 5 | A |
| 21 | polymer of exmaple 5 | methylene chloride | 5 | 32 | 3 | A |
| 22 | polymer of example 6 | toluene | 1 | 32 | 3 | A |
| 23 | polymer of example 7 | toluene | 0.5 | 32 | 3 | A |
| 24 | polymer of example 8 | methylene chloride | 0.5 | 32 | 3 | A |
| 25 | polymer of example 9 | methylene chloride | 0.5 | 23 | 5 | A |
| 26 | polymer of example 9 | toluene | 0.5 | 32 | 3 | A |
| 27 | polymer of example 10 | toluene | 0.5 | 32 | 3 | A |
| 28 | polymer of example 11 | methylene chloride | 0.5 | 32 | 3 | A |
| 29 | polymer of example 11 | toluene | 0.5 | 23 | 5 | A |
| 30 | polymer of example 11 | xylene | 0.5 | 32 | 3 | A |
| 31 | polymer of example 12 | methylene chloride | 0.5 | 32 | 3 | A |
| 32 | polymer of example 13 | methylene chloride | 0.5 | 32 | 3 | A |
| 33 | polymer of example 14 | methylene chloride | 1 | 32 | 3 | A |

Comparative Examples 1 to 5

Adhesives of compositions shown in Table 4 were prepared in accordance with the preparation methods of Examples 15 to 33. By using solutions of these adhesives, the adhering forces under the adhesion conditions shown in Table 4 were evaluated in compliance with the above-mentioned method of evaluation. The results were as shown in Table 4.

TABLE 4

| Comp. Ex. No. | Adhesive polymer | Solvent | Concentration (wt %) | Adhesion condition (preserved in water) Temp. (°C.) | Time (min) | Evaluation |
|---|---|---|---|---|---|---|
| 1 | polymer 1 | methylene chloride | 5 | 32 | 20 | D |
| 2 | polymer 2 | methylene chloride | 5 | 32 | 20 | D |
| 3 | DMS-M20H20 | methylene chloride | 5 | 32 | 20 | D |
| 4 | polymer 3 | methylene chloride | 10 | 60 | 20 | A |
| 5 | polymer 3 | methylene chloride | 10 | 32 | 20 | C | polymer 1: Copolymer of methyl methacrylate and

TABLE 4-continued

| Comp. Ex. No. | Adhesive polymer | Solvent | Concentration (wt %) | Adhesion condition (preserved in water) | | Evaluation |
|---|---|---|---|---|---|---|
| | | | | Temp. (°C.) | Time (min) | |

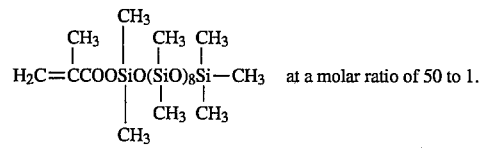 at a molar ratio of 50 to 1.

polymer 2: Copolymer of methyl methacrylate and allyl methacrylate at a molar ratio of 50 to 1.
polymer 3: Copolymer of methyl methacrylate and

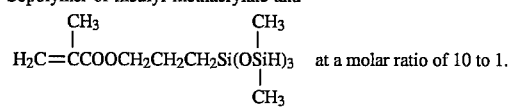 at a molar ratio of 10 to 1.

Comp. Ex.: Comparative Example

It will be understood From the results of Tables 3 and 4 that the adhesives (Examples 15 to 33) of the present invention exhibit sufficiently large adhering forces. According to Comparative Examples, on the other hand, adhesion was not quite accomplished when the copolymer did not have SiH reaction point on the polysiloxane moiety (Comparative Example 1), when the copolymer did not have a polysiloxane moiety (Comparative Example 2), and when the copolymer did not have a polymethacrylate moiety (Comparative Example 3). When the silicone-modified acrylic resin disclosed in Japanese Laid-Open Patent Publication No. 68007/1992 was used, adhesion was accomplished when it was heated (60° C.) (Comparative Example 4) but adhesion was not sufficient under a low-temperature condition (32° C.) (Comparative Example 5).

Example 34

27.4 Grams (9.8 mmols) of a DHS-M20H20, 300 ml of toluene and 0.33 g of a platinum/divinyl siloxane complex solution in which the amount of platinum had been adjusted to 1000 ppm were introduced into a flask, and were heated at 80° C. with stirring while bubbling nitrogen. A solution obtained by dissolving in 100 ml of toluene 5 g (0.98 meq - Vi/g) of a copolymer (weight average molecular weight, 102,000) of methyl methacrylate and allyl methacrylate at a copolymerization ratio of 50 to 1 (molar ratio), was added dropwise thereto over a period of one hour. After the dropwise addition had been finished, the mixture was heated and stirred for 6 hours, toluene was removed under reduced pressure, an excess of DHS-M20H20 was washed with a methanol/ethanol mixture solvent, followed by filtration and drying to obtain 6.8 g of a silicone-modified acrylic copolymer (yield, 87.9%). The obtained polymer possessed a weight average molecular weight of 160,000 with the polystyrene as a standard. It was confirmed through the H-NMR spectrum and ultimate analysis (C, H) that the obtained copolymer possessed the following structural units and the average recurring unit number

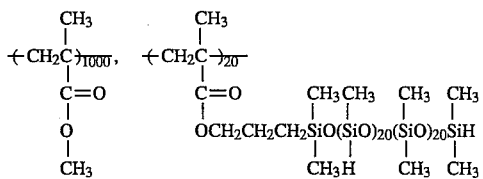

Figure 5:
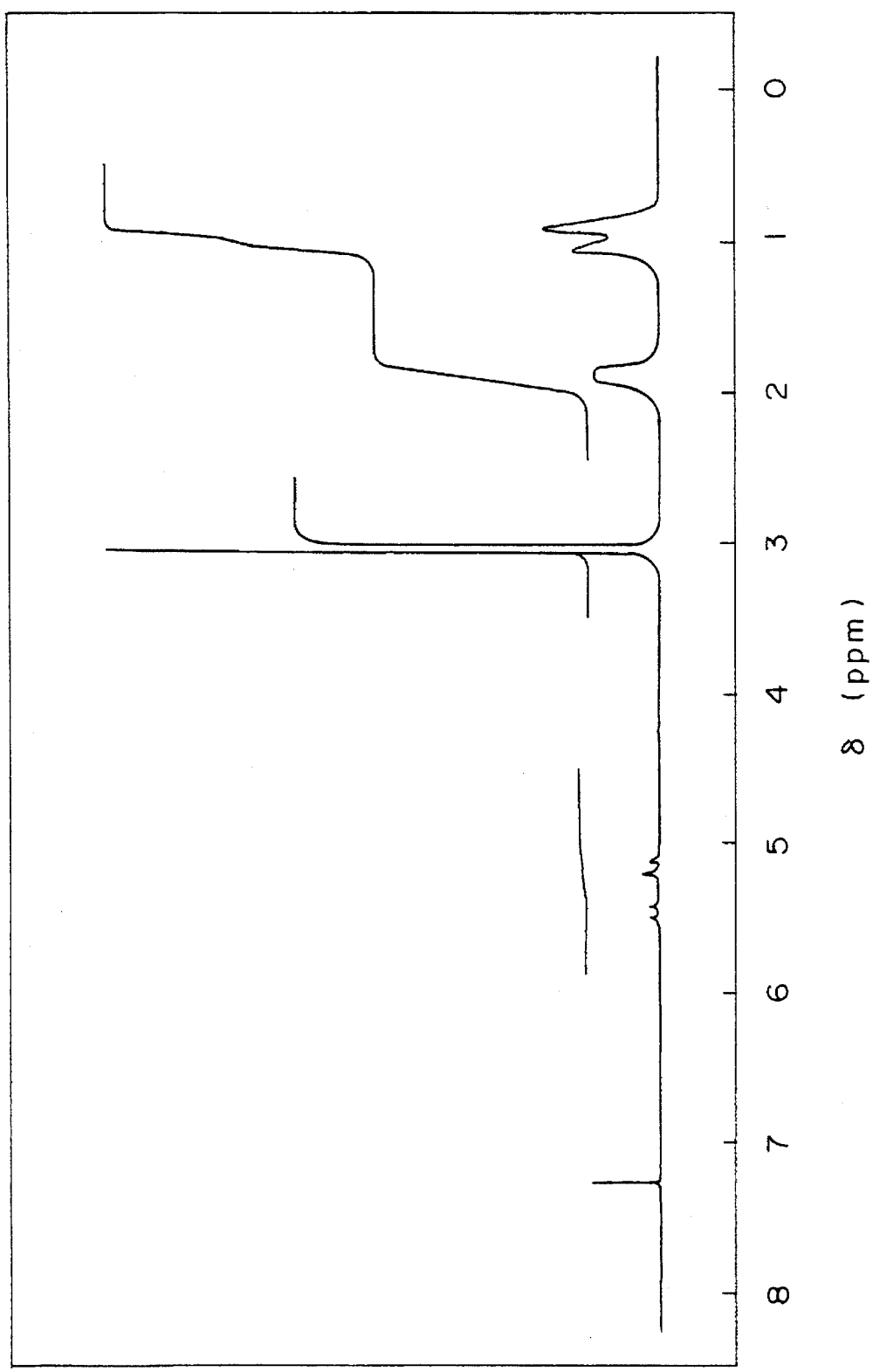
FIG. 5 is a diagram of magnetic resonance spectra ($^1$H-NMR spectra) of a polymethacrylate copolymer of before being modified with silicone used in Example 34.
Figure 6:
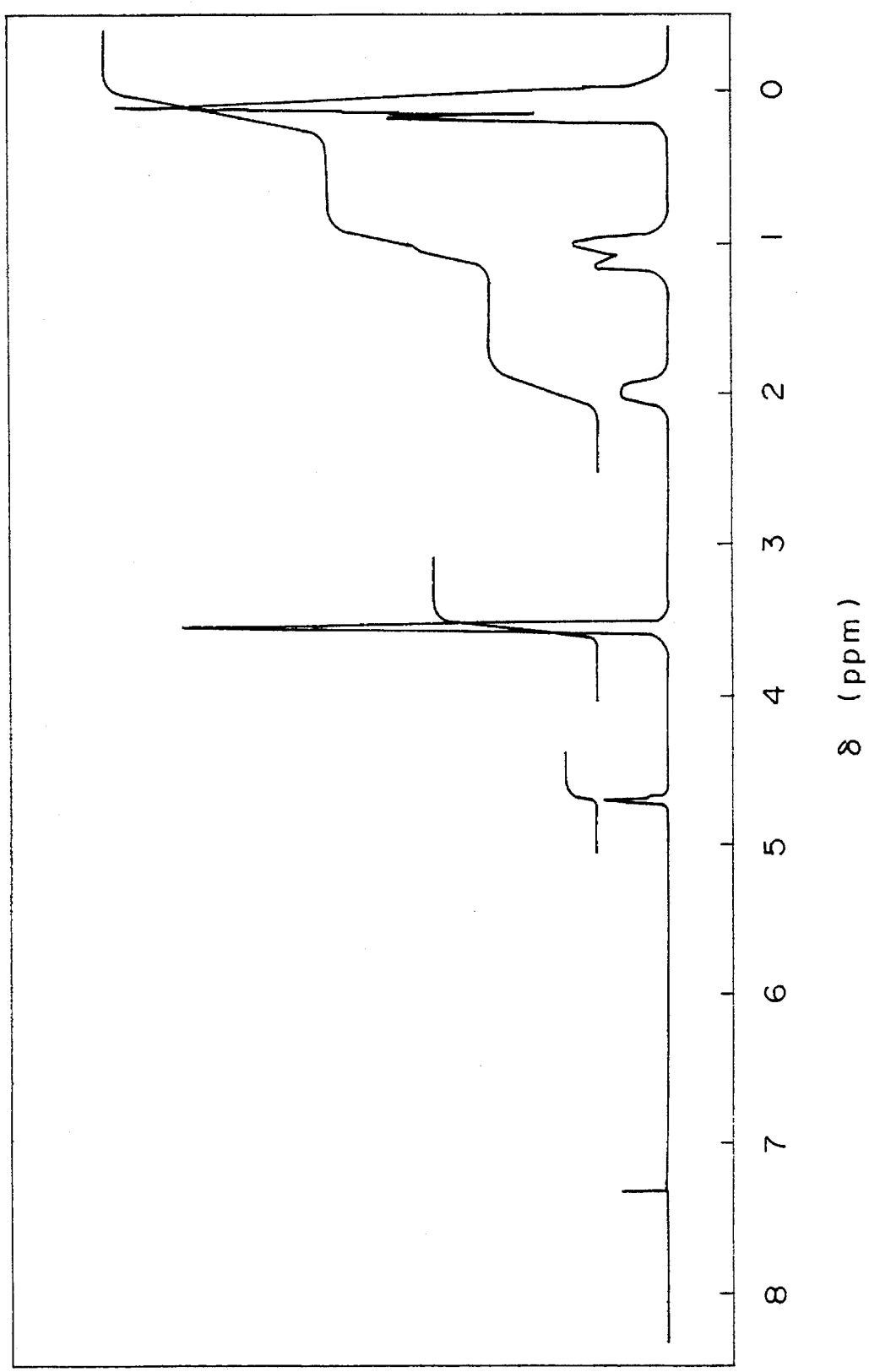
FIG. 6 is a diagram of magnetic resonance spectra ($^1$H-NMR spectra) of a silicone-modified acrylic copolymer obtained in Example 34.

H-NMR spectrum ($CHCl_3$ as a standard, δ ppm): FIG. 5 shows the spectra of a methacrylate polymer which is the synthesized starting material and FIG. 6 shows the spectra of the formed product.

From the spectra (FIG. 5), the methacrylate polymer which is the synthesized starting material exhibits broad absorptions over 0.5 to 1.2 ppm and 1.5 to 2.2 ppm, a single ray absorption by protons of the COO—$CH_3$ group at 3.5 ppm and multiple ray absorptions by protons of double bond of an allyl group at 5 to 6 ppm, whereas the spectra (FIG. 6) of the formed product exhibits no absorption by proton of the allyl group, but exhibits absorption by protons of the SiH group at 4.6 ppm, and absorption by protons of the Si—$CH_3$ group at 0.1 ppm. Moreover, the ratio of the strength of the single ray absorption by protons of the COO—$CH_3$ group at 3.5 ppm to the strength of absorption by protons of the Si—$CH_3$ group at 0.1 ppm (0.1 ppm/3.5 ppm, hereinafter abbreviated as S/PM=0.93) is 1.25 (S/PM=1.29 when they react equivalently), from which it is learned that the addition reaction of the DHS-M20H20 to the allyl group is carried out nearly equivalently.

Elementary analysis (C, H): C 48.58%, H 7.90% were in good agreement with the calculated values C 48.51%, H 7.86%.

Example 35

A silicone-modified acrylic copolymer was obtained through the same procedure as in Example 34 but using, as a starting material, a copolymer (weight average molecular weight, 100,000) of methyl methacrylate and allyl methacrylate at a copolymerization ratio of 100 to 1 (molar ratio) in an amount equal to the equivalent of vinyl groups instead of using the copolymer (weight average molecular weight, 102,000) of methyl methacrylate and allyl methacrylate at a copolymerization ratio of 50 to 1 (molar ratio). The obtained polymer possessed a weight average molecular weight of 130,000 with the polystyrene as a standard. It was confirmed through the H-NMR spectrum and ultimate analysis (C, H) that the obtained copolymer possessed the following structural units and the average recurring unit number

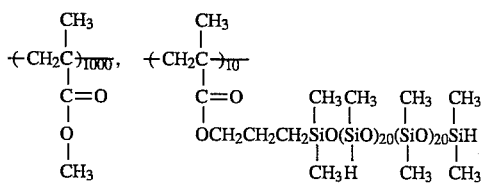

H-NMR spectra (CHCl$_3$ as a standard, δ ppm): The spectra were nearly the same as those shown in Example 34. The difference was only with respect to the area ratio of the peak due to the polysiloxane to the peak due to the polymethacrylate.

Ultimate analysis (C, H): C 53.00%, H 7.93% were in good agreement with the calculated values C 52.95%, H 7.91%.

Example 36

A silicone-modified acrylic copolymer was obtained through the same procedure as in Example 34 but using a DHS-M10H10P10 in an equal molar amount instead of using the DHS-M20H20. The obtained polymer possessed a weight average molecular weight of 160,000 with the polystyrene as a standard. It was confirmed through the H-NMR spectrum and ultimate analysis (C, H) that the obtained copolymer possessed the following structural units and the average recurring unit number

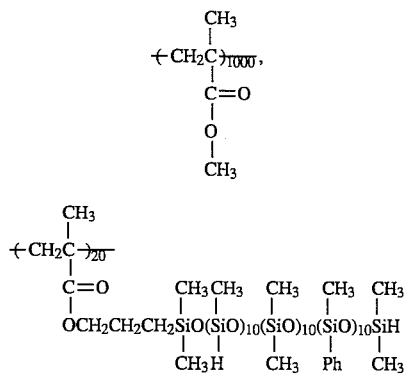

(wherein Ph denotes a phenyl group).

Figure 7:
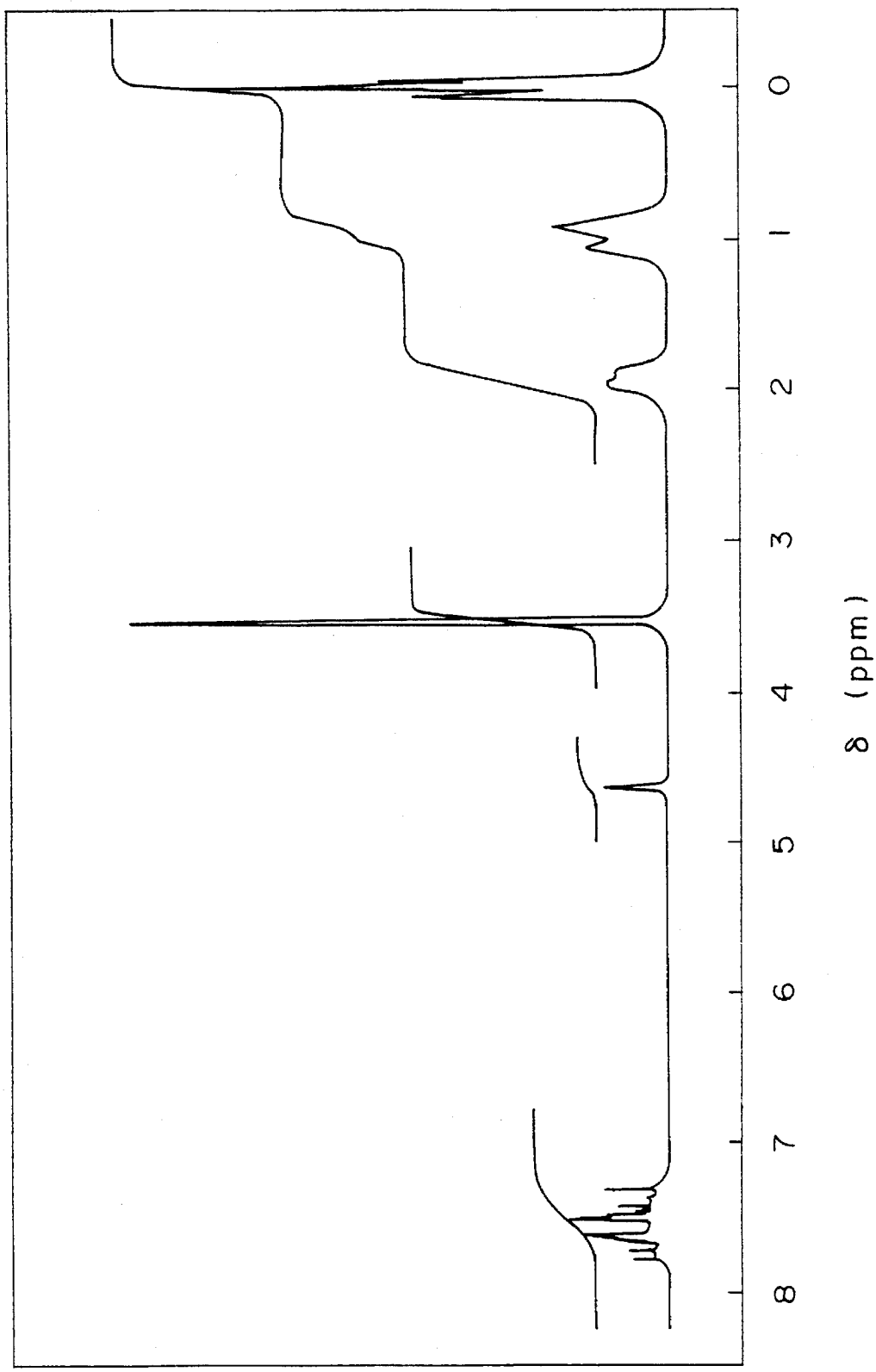
FIG. 7 is a diagram of magnetic resonance spectra ($^1$H-NMR spectra) of a silicone-modified acrylic copolymer obtained in Example 36.

H-NMR spectra (CHCl$_3$ as a standard, δ ppm): FIG. 7 shows the spectra of the formed product.

It will be understood from FIG. 7 that the absorption (5 to 6 ppm) by protons of the allyl group is extinguishing but there are appearing absorption by protons of the SiH group at 4.6 ppm, absorption by protons of the Si—CH$_3$ group at 0.1 ppm and multiple line absorption by protons of Si—Ph (Ph is a phenyl group) at 7 to 8 ppm.

Ultimate analysis (C, H): C 54.50%, H 7.66% were in good agreement with the calculated values C 54.44%, H 7.59%.

Example 37

A silicone-modified acrylic copolymer was obtained through the same procedure as in Example 34 but using, as a starting material, a copolymer (weight average molecular weight, 35,000) of methyl acrylate and allyl acrylate at a copolymerization ratio of 15 to 1 (molar ratio) in an amount equal to the equivalent of vinyl groups instead of using the copolymer (weight average molecular weight, 102,000) of methyl methacrylate and allyl methacrylate at a copolymerization ratio of 50 to 1 (molar ratio) and using DHS-H20 in an equal molar amount instead of using the DHS-M20H20. The obtained polymer possessed a weight average molecular weight of 62,000 with the polystyrene as a standard. It was confirmed through the H-NMR spectrum and ultimate analysis (C, H) that the obtained copolymer possessed the following structural units and the average recurring unit number

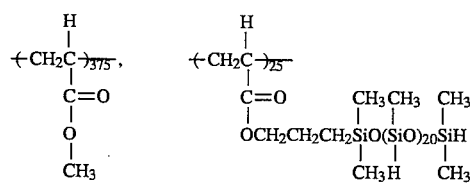

Example 38

A silicone-modified acrylic copolymer was obtained through the same procedure as in Example 34 but using, as a starting material, a copolymer (weight average molecular weight, 80,000) of propyl methacrylate and allyl methacrylate at a copolymerization ratio of 30 to 1 (molar ratio) in an amount equal to the equivalent of vinyl groups instead of using the copolymer (weight average molecular weight, 102,000) of methyl methacrylate and allyl methacrylate at a copolymerization ratio of 50 to 1 (molar ratio) and using MHS-M20H20 in an equal molar amount instead of using the DHS-M20H20. The obtained polymer possessed a weight average molecular weight of 136,000 with the polystyrene as a standard. It was confirmed through the H-NMR spectrum and ultimate analysis (C, H) that the obtained copolymer possessed the following structural units and the average recurring unit number

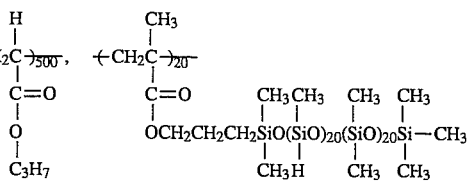

Example 39

A silicone-modified acrylic copolymer was obtained through the same procedure as in Example 34 but using, as a starting material, a copolymer (weight average molecular weight, 77,000) of methyl methacrylate and allyl methacrylate at a copolymerization ratio of 50 to 1 (molar ratio) in an amount equal to the equivalent of vinyl groups instead of using the copolymer (weight average molecular weight, 102,000) of methyl methacrylate and allyl methacrylate at a copolymerization ratio of 50 to 1 (molar ratio) and using DHS-P20H20 in an equal molar amount instead of using the DHS-M20H20. The obtained polymer possessed a weight average molecular weight of 140,000 with the polystyrene as a standard. It was confirmed through the H-NMR spectrum and ultimate analysis (C, H) that the obtained copolymer possessed the following structural units and the average recurring unit number

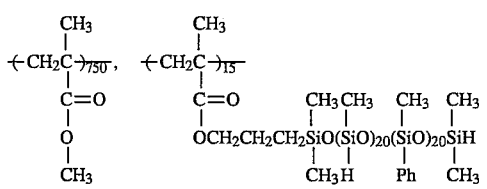

(wherein Ph is a phenyl group).

Example 40

A silicone-modified acrylic copolymer was obtained through the same procedure as in Example 34 but using, as a starting material, a copolymer (weight average molecular weight, 63,000) of methyl methacrylate and triethylene glycol monoallyl ether ester of methacrylic acid at a copolymerization ratio of 50 to 1 (molar ratio) in an amount equal to the equivalent of vinyl groups instead of using the copolymer (weight average molecular weight, 102,000) of methyl methacrylate and allyl methacrylate at a copolymerization ratio of 50 to 1 (molar ratio). The obtained polymer possessed a weight average molecular weight of 95,000 with the polystyrene as a standard. It was confirmed through the H-NMR spectrum and ultimate analysis (C, H) that the obtained copolymer possessed the following structural units and the average recurring unit number

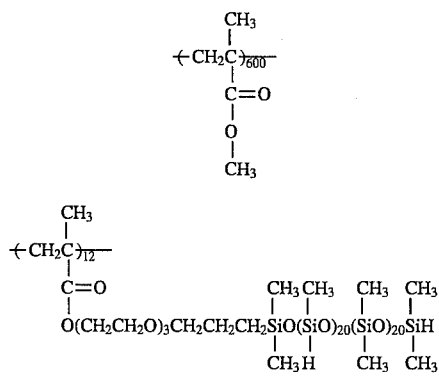

Example 41

5 Grams (0.98 meq - Vi/g) of a copolymer (weight average molecular weight, 51,000) of a methyl methacrylate and allyl methacrylate at a copolymerization ratio of 50 to 1 (molar ratio), 13.7 g (4.9 mmols) of a DHS-M20H20, 150 ml of toluene, and 0.39 g of a platinum/divinyl siloxane complex solution in which the amount of platinum had been adjusted to 100 ppm were fed into a flask and were heated at 80° C. with stirring while bubbling nitrogen. After two hours had passed, the reaction was terminated, toluene was removed under reduced pressure, the excess of DHS-M20H20 was washed with hexane, followed by filtration and drying to obtain a silicone-modified acrylic copolymer in an amount of 6.2 g (yield, 80.1%). The obtained polymer possessed a weight average molecular weight of 65,000 with the polystyrene as a standard. It was confirmed through the H-NMR spectrum and ultimate analysis (C, H) that the obtained copolymer possessed the following structural units and the average recurring unit number

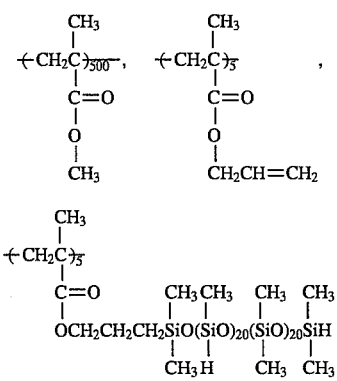

Figure 8:
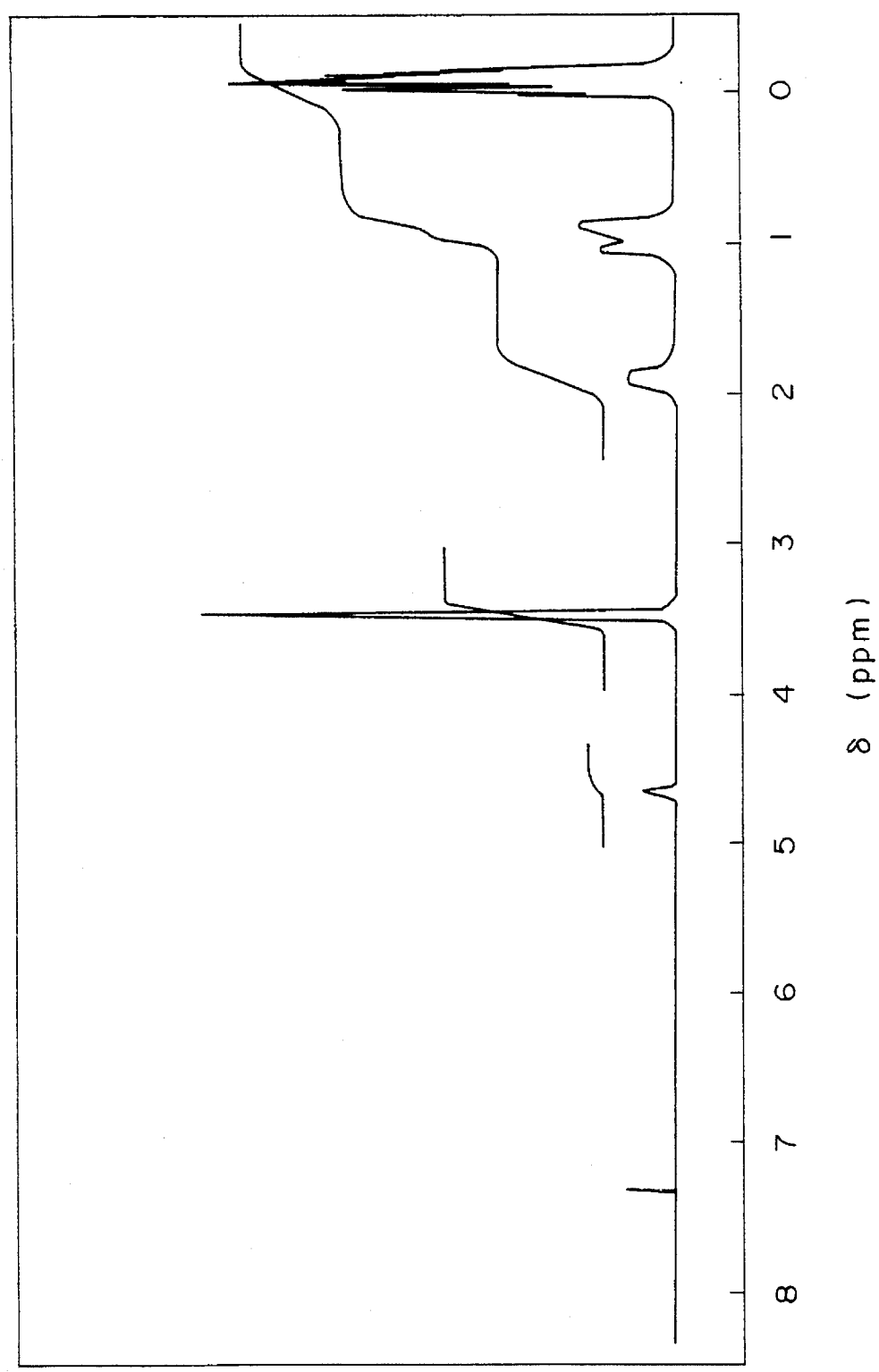
FIG. 8 is a diagram of magnetic resonance spectra ($^1$H-NMR spectra) of a silicone-modified acrylic copolymer obtained in Example 41.

H-NMR spectra (CHCl$_3$ as a standard, δ ppm): FIG. 8 shows the spectra of the formed product.

The addition conversion of DHS-M20H20 to the allyl group was calculated from S/PM (0.63) of FIG. 8 (S/PM= 1.29 when they react equivalently) (conversion, 50.0%).

Ultimate analysis (C, H): C 52.91%, H 7.88% were in good agreement with the calculated values C 53.08%, H 7.91%.

Example 42

A silicone-modified acrylic copolymer was obtained through the same procedure as in Example 41 but using, as a starting material, a copolymer (weight average molecular weight, 55,000) of methyl methacrylate and vinyl methacrylate at a copolymerization ratio of 50 to 1 (molar ratio) in an amount equal to the equivalent of vinyl groups instead of using the copolymer (weight average molecular weight, 51,000) of methyl methacrylate and allyl methacrylate at a copolymerization ratio of 50 to 1 (molar ratio). The obtained polymer possessed a weight average molecular weight of 70,000 with the polystyrene as a standard. It was confirmed through the H-NMR spectrum and ultimate analysis (C, H) that the obtained copolymer possessed the following structural units and the average recurring unit number.

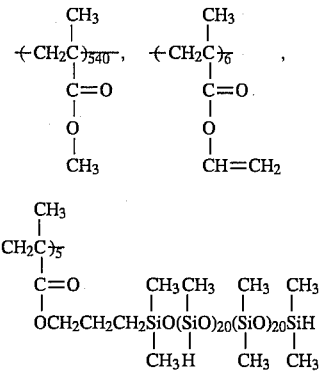

Example 43

A silicone-modified acrylic copolymer was obtained through the same procedure as in Example 41 but using, as a starting material, a copolymer (weight average molecular weight, 15,000) of methyl methacrylate and allyl methacrylate at a copolymerization ratio of 50 to 1 (molar ratio) in an amount equal to the equivalent of vinyl groups instead of using the copolymer (weight average molecular weight, 51,000) of methyl methacrylate and allyl methacrylate at a copolymerization ratio of 50 to 1 (molar ratio). The obtained polymer possessed a weight average molecular weight of 21,000 with the polystyrene as a standard. It was confirmed through H-NMR spectrum and ultimate analysis (C, H) that the obtained copolymer possessed the following structural units and the average recurring unit number.

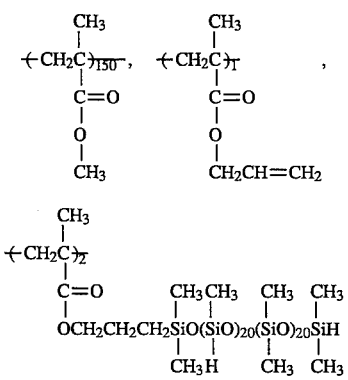

Example 44

A silicone-modified acrylic copolymer was obtained through the same procedure as in Example 41 but using, as a starting material, a copolymer (weight average molecular weight, 63,000) of methyl methacrylate and allyl methacrylate at a copolymerization ratio of 5 to 1 (molar ratio) in an amount equal to the equivalent of vinyl groups instead of using the copolymer (weight average molecular weight, 51,000) of methyl methacrylate and allyl methacrylate at a copolymerization ratio of 50 to 1 (molar ratio). The obtained polymer possessed a weight average molecular weight of 90,000 with the polystyrene as a standard. It was confirmed through H-NMR spectrum and ultimate analysis (C, H) that the obtained copolymer possessed the following structural units and the average recurring unit number.

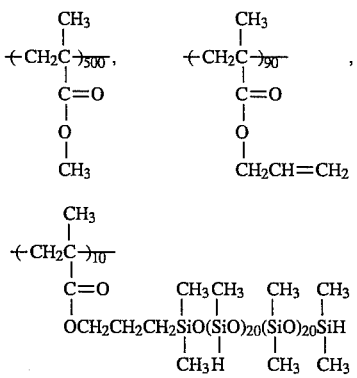

Example 45

A silicone-modified acrylic copolymer was obtained through the same procedure as in Example 41 but using, as a starting material, a copolymer (weight average molecular weight, 64,000) of methyl methacrylate, benzyl methacrylate, 9-decenyl methacrylate and oleyl methacrylate at a copolymerization ratio of 80 to 20 to 4 to 1 (molar ratio) in an amount equal to the equivalent of vinyl groups instead of using the copolymer (weight average molecular weight, 51,000) of methyl methacrylate and allyl methacrylate at a copolymerization ratio of 50 to 1 (molar ratio). The obtained polymer possessed a weight average molecular weight of 92,000 with the polystyrene as a standard. It was confirmed through H-NMR spectrum and ultimate analysis (C, H) that the obtained copolymer possessed the following structural units and the average recurring unit number.

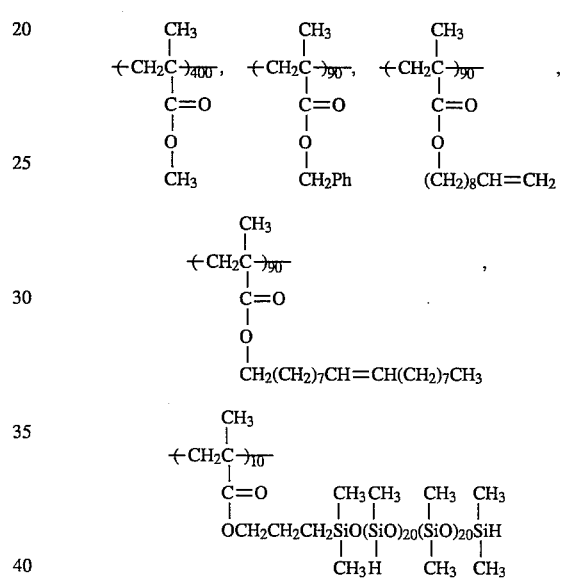

Weight average molecular weights and values of ultimate analyses of the silicone-modified acrylic copolymers synthesized in Examples 34 to 45 are shown in Table 5.

TABLE 5

| Example No. | Weight average molecular weight (polystyrene as a standard) | Ultimate analysis (wt %)* | |
|---|---|---|---|
| | | C | H |
| 34 | 160000 | 48.58 (48.51) | 7.90 (7.86) |
| 35 | 130000 | 53.00 (52.95) | 7.93 (7.91) |
| 36 | 160000 | 54.50 (54.44) | 7.66 (7.59) |
| 37 | 62000 | 44.25 (44.17) | 7.95 (7.85) |
| 38 | 136000 | 49.88 (49.81) | 8.66 (8.63) |
| 39 | 140000 | 55.08 (55.03) | 7.27 (7.23) |
| 40 | 95000 | 48.63 (48.61) | 7.89 (7.88) |
| 41 | 65000 | 52.91 (53.08) | 7.88 (7.91) |
| 42 | 70000 | 53.54 (53.44) | 8.01 (7.90) |
| 43 | 21000 | 51.41 | 7.99 |

TABLE 5-continued

| Example No. | Weight average molecular weight (polystyrene as a standard) | Ultimate analysis (wt %)* | |
|---|---|---|---|
| | | C | H |
| 44 | 90000 | (51.36) 50.66 (50.78) | (7.89) 7.70 (7.87) |
| 45 | 92000 | 54.00 (53.93) | 7.95 (7.86) |

*Calculated values are in parentheses

Evaluation of Adhering Force

Example 46

An adhesive was prepared by dissolving the copolymer synthesized in Example 34 in an amount of 0.5% by weight in the methylene chloride. By using a small brush, the adhesive was applied onto the acrylic plate and was dried for about one minute. The aforementioned addition-type silicone pastes A and B which are test materials were well kneaded together in an equal amount, and were thickly applied onto the acrylic plate on which the adhesive solution had been applied. The acrylic plate was left to stand still in the water maintained at 32° C. for three minutes, and was taken out to evaluate the adhering force in compliance with the method of evaluation mentioned earlier. The result was A.

Examples 47 to 62

Adhesives of compositions shown in Table 6 were prepared by using silicone-modified acrylic copolymers synthesized in Examples 34 to 45 according to the preparation method of Example 34. These adhesives were evaluated for their adhering force under the adhesion conditions shown in Table 6 in accordance with the above-mentioned method of evaluation. The results were as shown in Table 6.

TABLE 6

| Example No. | Adhesive polymer (synthesized in Examples 34–45) | Solvent | Concentration (wt %) | Adhesion condition (preserved in water) | | Evaluation |
|---|---|---|---|---|---|---|
| | | | | Temp. (°C.) | Time (min) | |
| 46 | polymer of example 34 | methylene chloride | 0.5 | 32 | 5 | A |
| 47 | polymer of example 34 | methylene chloride | 0.5 | 25 | 3 | A |
| 48 | polymer of example 34 | methylene chloride | 10 | 32 | 3 | A |
| 49 | polymer of example 34 | toluene | 0.5 | 32 | 3 | A |
| 50 | polymer of example 35 | methylene chloride | 0.5 | 32 | 3 | A |
| 51 | polymer of example 36 | methylene chloride | 0.5 | 32 | 3 | A |
| 52 | polymer of example 37 | methylene chloride | 10 | 32 | 3 | A |
| 53 | polymer of example 38 | methylene chloride | 5 | 32 | 3 | A |
| 54 | polymer of example 39 | toluene | 1 | 32 | 3 | A |
| 55 | polymer of example 40 | toluene | 0.5 | 32 | 3 | A |
| 56 | polymer of example 41 | methylene chloride | 0.5 | 25 | 3 | A |
| 57 | polymer of example 41 | tetrahydrofurane | 0.5 | 32 | 3 | A |
| 58 | polymer of example 41 | toluene | 0.5 | 32 | 3 | A |
| 59 | polymer of example 42 | methylene chloride | 0.5 | 32 | 3 | A |
| 60 | polymer of example 43 | methylene chloride | 1.0 | 32 | 3 | A |
| 61 | polymer of example 44 | toluene | 0.5 | 32 | 3 | A |
| 62 | polymer of example 45 | methylene chloride | 0.5 | 32 | 3 | A |

Comparative Examples 6 to 10

Adhesives of compositions shown in Table 7 were prepared in accordance with the preparation methods of examples 47 to 62. By using solutions of these adhesives, the adhering forces under the adhesion conditions shown in Table 7 were evaluated in compliance with the above-mentioned method of evaluation. The results were as shown in Table 7.

TABLE 7

| Comp. Ex. No. | Adhesive polymer | Solvent | Concentration (wt %) | Adhesion condition (preserved in water) Temp. (°C.) | Time (min) | Evaluation |
|---|---|---|---|---|---|---|
| 6 | polymer 1 | methylene chloride | 5 | 32 | 20 | D |
| 7 | polymer 2 | methylene chloride | 5 | 32 | 20 | D |
| 8 | DMS-M20H20 | methylene chloride | 5 | 32 | 20 | D |
| 9 | polymer 3 | methylene chloride | 10 | 60 | 20 | A |
| 10 | polymer 3 | methylene chloride | 10 | 32 | 20 | C | polymer 1: Copolymer of methyl methacrylate and

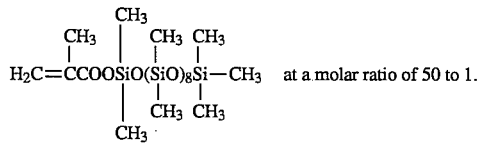

at a molar ratio of 50 to 1.

polymer 2: Copolymer of methyl methacrylate and allyl methacrylate at a molar ratio of 50 to 1.
polymer 3: Copolymer of methyl methacrylate and

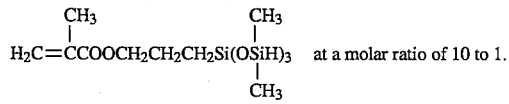

at a molar ratio of 10 to 1.

Comp. Ex.: Comparative Example

It will be understood From the results of Tables 6 and 7 that the adhesives (Examples 56 to 62) of the present invention exhibit sufficiently large adhering forces. According to Comparative Examples, on the other hand, adhesion was not quite accomplished when the copolymer did not have SiH reaction point on the polysiloxane moiety (Comparative Example 6), when the copolymer did not have a polysiloxane moiety (Comparative Example 7), and when the copolymer did not have a polymethacrylate moiety (Comparative Example 8). When the silicone-modified acrylic resin disclosed in Japanese Laid-Open Patent Publication No. 68007/1992 was used, adhesion was accomplished when it was heated (60° C.) (Comparative Example 9) but adhesion was not sufficient under a low-temperature condition (32° C.) (Comparative Example 10).

We claim:
1. A silicone-modified acrylic copolymer comprising:
I. a structural unit of the formula

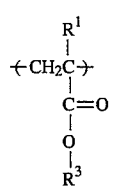

(1)

wherein $R^1$ is a hydrogen atom, a methyl group or an ethyl group, and $R^3$ is an alkyl group with 1 to 13 carbon atoms or an aryl group with 6 to 14 carbon atoms, II. a structural unit of the formula

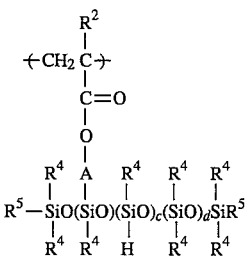

(2a)

or of the formula

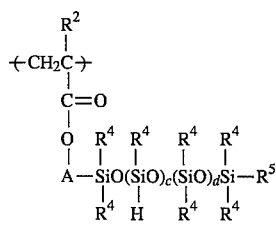

(2b)

wherein $R^2$ is a hydrogen atom, a methyl group or an ethyl group, each of $R^4$ is an alkyl group with 1 to 6 carbon atoms or an aryl group with 6 to 14 carbon atoms which may be the same or different, each of $R^5$ is a hydrogen atom, an alkyl group with 1 to 6 carbon atoms or an aryl group with 6 to 14 carbon atoms which may be the same or different, A is a divalent organic group with 2 to 20 carbon atoms which may have an ether bond or an ester bond in the main chain, and c and d are average recurring unit numbers, c being a number of 1 to 100 and d being a number of 0 to 100, and III. a structural unit of the formula

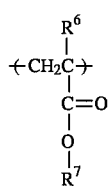 (3)

wherein $R^6$ is a hydrogen atom, a methyl group or an ethyl group, and $R^7$ is an ethylenically unsaturated hydrocarbon group with 2 to 20 carbon atoms which may have an ether bond or an ester bond in the main chain, wherein the unit (I), the unit (II) and the unit (III) are contained at ratios in mole % of (I)=10 to 99.9, (II)=90 to 0.1, and (III)=0 to 89.9, and have weight average molecular weights of from 5,000 to 1,000,000.

2. A silicone-modified acrylic copolymer according to claim 1, wherein $R^1$, $R^2$ and $R^6$ in the structural units (1) to (3) are hydrogen atoms or methyl groups.

3. A silicone-modified acrylic copolymer according to claim 1, wherein $R^3$ in the structural unit (1) is an alkyl group with 1 to 3 carbon atoms.

4. A silicone-modified acrylic copolymer according to claim 1, wherein $R^4$ in the structural unit (2a) or (2b) is a methyl group or a phenyl group.

5. A silicone-modified acrylic copolymer according to claim 1, wherein $R^5$ in the structural unit (2a) or (2b) is a hydrogen atom, a methyl group or a phenyl group.

6. A silicone-modified acrylic copolymer according to claim 1, wherein $R^7$ in the structural unit (3) is an ethylenically unsaturated hydrocarbon group with 3 to 10 carbon atoms.

7. A silicone-modified acrylic copolymer according to claim 1, wherein the group A in the structural unit (2a) or (2b) is a divalent saturated hydrocarbon group with 3 to 10 carbon atoms.

8. A silicone-modified acrylic copolymer according to claim 1, wherein said silicone-modified acrylic copolymer has three or more SiH groups per a unit of a polyorganosiloxane group in the silicone-modified acrylic copolymer.

9. An adhesive obtained by dissolving the silicone-modified acrylic copolymer of claim 1 in a solvent in which said copolymer is soluble.

10. An adhesive according to claim 9, wherein said soluble solvent is methylene chloride or toluene.

11. An adhesive according to claim 9, wherein the adhesive contains the silicone-modified acrylic copolymer in an amount of from 0.1 to 20% by weight.

12. The silicone-modified acrylic copolymer of claim 1 wherein the unit (I), the unit (II) and the unit (III) are present at ratios of (I) 50 to 99.9 mole %, (II) 50 to 0.1 mole %, and (III) 0 to 49.9 mole %.

13. The silicone-modified acrylic copolymer of claim 12 wherein structural units of formula (3) are present.

14. The silicone-modified acrylic copolymer of claim 12 wherein structural units of formula (3) are absent.

15. The silicone-modified acrylic copolymer of claim 1 wherein in the formula (2a) and (2b) c and d satisfy the relationships $10 \leq c+d \leq 100$ and $0 \leq d/c \leq 10$.

16. A silicone-modified acrylic copolymer according to claim 2, wherein $R^3$ in the structural unit (1) is an alkyl group with 1 to 3 carbon atoms, $R^4$ in the structural units (2a) and (2b) is a methyl or phenyl group, $R^5$ in the structural units (2a) and (2b) is a hydrogen atom, a methyl group or a phenyl group, $R^7$ in the structural unit (3) is an ethylenically unsaturated hydrocarbon group with 3 to 10 carbon atoms, and A in structural units (2a) and (2b) is a divalent saturated hydrocarbon group with 3 to 10 carbon atoms.

17. The silicone-modified acrylic copolymer of claim 16 which has at least 3 SiH groups per unit of polyorganosiloxane group in the copolymer.

18. The silicone-modified acrylic copolymer of claim 16 wherein structural units of formula (3) are present.

19. The adhesive according to claim 10, wherein the silicone-modified acrylic copolymer is present in an amount of from 0.1 to 20% by weight.

* * * * *